US009105410B2

(12) United States Patent
Wonneberger et al.

(10) Patent No.: US 9,105,410 B2
(45) Date of Patent: Aug. 11, 2015

(54) BORON CONTAINING PERYLENE MONOIMIDES, A PROCESS FOR THEIR PRODUCTION, THEIR USE AS BUILDING BLOCKS FOR THE PRODUCTION OF PERYLENE MONOIMIDE DERIVATIVES, MONOIMIDE DERIVATIVES AND THEIR USE IN DYE-SENSITIZED SOLAR CELLS

(71) Applicants: BASF SE, Ludwigshafen (DE); Max-Planck-Gesellschaft zur Foerd. der Wisse e.V., Munich (DE)

(72) Inventors: Henrike Wonneberger, Mannheim (DE); Ingmar Bruder, Mutterstadt (DE); Robert Send, Karlsruhe (DE); Glauco Battagliarin, Mannheim (DE); Chen Li, Cologne (DE); Klaus Muellen, Cologne (DE)

(73) Assignees: BASF SE, Ludwigshafen (DE); MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 0 days.

(21) Appl. No.: 14/336,580

(22) Filed: Jul. 21, 2014

(65) Prior Publication Data
US 2014/0357867 A1 Dec. 4, 2014

Related U.S. Application Data

(62) Division of application No. 13/958,934, filed on Aug. 5, 2013, now Pat. No. 8,816,081.

(60) Provisional application No. 61/679,827, filed on Aug. 6, 2012.

(51) Int. Cl.
C07D 221/22 (2006.01)
C07D 493/00 (2006.01)
H01L 31/00 (2006.01)
H01G 9/20 (2006.01)
C07D 221/18 (2006.01)
H01L 51/00 (2006.01)
C07F 5/04 (2006.01)
C09B 5/62 (2006.01)

(52) U.S. Cl.
CPC ............ *H01G 9/2059* (2013.01); *C07D 221/18* (2013.01); *C07F 5/04* (2013.01); *C09B 5/62* (2013.01); *H01L 51/006* (2013.01); *H01L 51/0053* (2013.01); *H01G 9/2031* (2013.01); *H01L 51/008* (2013.01); *Y02B 10/10* (2013.01); *Y02E 10/542* (2013.01); *Y02E 10/549* (2013.01)

(58) Field of Classification Search
USPC .......... 546/58, 13, 38; 549/232, 213; 136/252
See application file for complete search history.

(56) References Cited

U.S. PATENT DOCUMENTS

| 4,927,721 | A | 5/1990 | Gratzel et al. |
|---|---|---|---|
| 5,350,644 | A | 9/1994 | Graetzel et al. |
| 5,405,962 | A * | 4/1995 | Muellen et al. ................. 546/27 |
| 7,799,920 | B2 | 9/2010 | Koenemann et al. |
| 8,119,802 | B2 | 2/2012 | Moonen et al. |
| 8,471,020 | B2 | 6/2013 | Reichelt et al. |
| 2008/0114170 | A1 | 5/2008 | Konemann et al. |
| 2008/0269485 | A1 | 10/2008 | Moonen et al. |
| 2010/0022021 | A1 | 1/2010 | Gessner et al. |

FOREIGN PATENT DOCUMENTS

| CN | 101056860 A | 10/2007 |
|---|---|---|
| CN | 101730723 A | 6/2010 |
| EP | 1 176 646 A1 | 1/2002 |
| JP | 10-189065 | 7/1998 |
| JP | 10-334954 | 12/1998 |
| JP | 2000-100484 | 4/2000 |
| JP | 2000-243463 | 9/2000 |
| JP | 2001-93589 | 4/2001 |
| WO | WO 2007/054470 A1 | 5/2007 |
| WO | WO 2012/001628 A1 | 1/2012 |

OTHER PUBLICATIONS

International Search Report issued Jan. 23, 2014 in PCT/IB2013/056070.
Brian O'Regan, et al., "A low-cost, high-efficiency solar cell based on dye-sensitized colloidal $TiO_2$ films", Nature, vol. 353, 1991, pp. 737-740.
U. Bach, et al., "Solid-state dye-sensitized mesoporous $TiO_2$ solar cells with high photon-to-electron conversion efficiencies", Nature, vol. 395, 1998, pp. 583-585.
Mohammad K. Nazeeruddin, et al., "Combined Experimental and DFT-TDDFT Computational Study of Photoelectrochemical Cell Ruthenium Sensitizers", J. Am. Chem. Soc., vol. 127, 2005, pp. 16835-16847.
Yasuo Chiba, et al., "Dye-Sensitized Solar Cells with Conversion Efficiency of 11.1%", Jpn. J. Appl. Phys., vol. 45, No. 25, 2006, pp. L638-L640.
Feifei Gao, et al., "Enhance the Optical Absorptivity of Nanocrystalline $TiO_2$ Film with High Molar Extinction Coefficient Ruthenium Sensitizers for High Performance Dye-Sensitized Solar Cells", J. Am. Chem. Soc., vol. 130, 2008, pp. 10720-10728.

(Continued)

*Primary Examiner* — Charanjit Aulakh
(74) *Attorney, Agent, or Firm* — Oblon, McClelland, Maier & Neustadt, L.L.P.

(57) ABSTRACT

Boron-comprising perylene monoimides and a process for producing the boron-comprising perylene monoimides are provided. The boron-comprising perylene monoimides are useful as building blocks for producing perylene monoimide derivatives and monoimide derivatives. The boron-comprising perylene monoimides are also useful for preparing dye-sensitized solar cells.

6 Claims, No Drawings

(56) References Cited

OTHER PUBLICATIONS

Yiming Cao, et al., "Dye-Sensitized Solar Cells with a High Absorptivity Ruthenium Sensitizers Featuring a 2-(Hexylthio)thiophene Conjugated Bipyridine", J. Phys. Chem. C, vol. 113, 2009, pp. 6290-6297.

Chia-Yuan Chen, et al., "Highly Efficient Light-Harvesting Ruthenium Sensitizer for Thin-Film Dye-Sensitized Solar Cells", ACS Nano, vol. 3, No. 10, 2009, pp. 3103-3109.

Gopal K. Mor, et al., "Visible to Near-Infrared Light Harvesting in $TiO_2$ Nanotube Array—P3HT Based Heterojunction Solar Cells", Nano Letters, vol. 9, No. 12, 2009, pp. 4250-4257.

Henry J. Snaith, et al., "Efficiency Enhancements in Solid-State Hybrid Solar Cells via Reduced Charge Recombination and Increased Light Capture", Nano Letters, vol. 7, No. 11, 2007, pp. 3372-3376.

Suzanne Ferrere, et al., "New perylenes for dye sensitization of $TiO_2$", New J. Chem., vol. 26, 2002, pp. 1155-1160.

David N. Coventry, et al., "Selective Ir-catalysed borylation of polycyclic aromatic hydrocarbons: structures of naphthalene-2,6-bis(boronate), pyrene-2,7-bis(boronate) and perylene-2,5,8,11-tetra(boronate) esters", Chem. Commun., 2005, pp. 2172-2174.

Takuro Teraoka, et al., "Iridium-Catalyzed Direct Tetraborylation of Perylene Bisimides", Organic Letters, vol. 13, No. 10, 2011, pp. 2532-2535.

Glauco Battagliarin, et al., "2,5,8,11-Tetraboronic Ester Perylenediimides: A Next Generation Building Block for Dye-Stuff Synthesis", Organic Letters, vol. 13, No. 12, 2011, pp. 3012-3015.

Glauco Battagliarin, et al., "Efficient Tuning of LUMO Levels of 2,5,8,11-Substituted Perylenediimides via Copper Catalyzed Reactions", Organic Letters, vol. 13, No. 13, 2011, pp. 3399-3401.

Anil S. Guram, et al., "A Simple Catalytic Method for the Conversion of Aryl Bromides to Arylamines", Angew. Int. Ed. Engl., vol. 34, No. 12, 1995 pp. 1348-1350.

\* cited by examiner

BORON CONTAINING PERYLENE MONOIMIDES, A PROCESS FOR THEIR PRODUCTION, THEIR USE AS BUILDING BLOCKS FOR THE PRODUCTION OF PERYLENE MONOIMIDE DERIVATIVES, MONOIMIDE DERIVATIVES AND THEIR USE IN DYE-SENSITIZED SOLAR CELLS

This application is a divisional application of U.S. Ser. No. 13/958,934 filed on Aug. 5 2013, which claims the benefit of priority to U.S. 61/679,827 filed on Aug. 6, 2012.

Description

The present invention relates to compounds of general formula I

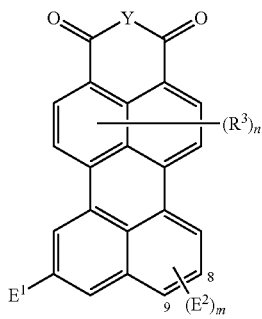

(I)

wherein the variables have the following meaning $E^1$, $E^2$ a moiety of formula Ia

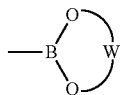

(Ia)

m 0 or 1, where in the case of m equal 1 $E^2$ is bound either to the 8 or 9 position of the perylene skeleton and is identical to $E^1$, W a bridging $C_2$ or $C_3$ moiety which may be substituted by one or more alkyl, $R^3$ identical or different radicals hydrogen, alkyl, cycloalkyl, aryl, hetaryl, alkoxy, aryloxy, arylthio, hetaryloxy, hetarylthio, diarylamino or dialkylamino, n 0, 1, 2, 3 or 4

Y oxygen or $NR^{12}$, and $R^{12}$ hydrogen, alkyl, cycloalkyl, aryl or hetaryl, or a moiety of formula —Z-A, wherein A is —COOM, —$SO_3M$ or —$PO_3M$, M hydrogen, alkali metal cation or $[NR']^{4+}$, R' hydrogen or alkyl, where the radicals R' may be identical or different, and Z $C_1$-$C_6$-alkylene or 1,4-phenylene, where the phenylene radical may be substituted by one or more substituents alkyl, nitro, cyano and/or halogen, and a process for the preparation of compounds of general formula I;

to a process for the preparation of compounds of general formula II

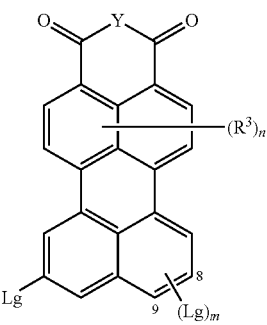

(II)

wherein the variables have the following meaning

Lg leaving group, m 0 or 1, where in the case of m equal 1 the one Lg is bound either to the 8 or 9 position of the perylene skeleton and is identical to the Lg bound to the 11 position, and the remaining variables $R^3$, n and Y have the abovementioned meaning, and to compounds of general formula II per se;

to a process for the preparation of compounds of general formula III

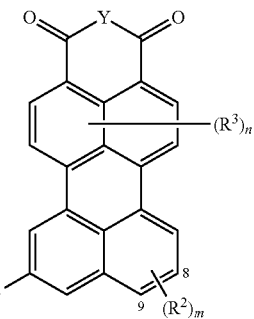

(III)

wherein the variables have the following meaning $R^1$, $R^2$ independently of each other a moiety of formula IIIa

(IIIa)

$R^4$, $R^5$ independently of each other aryl or hetaryl, m 0 or 1, where in the case of m equal 1 $R^2$ is bound either to the 8 or 9 position of the perylene skeleton, and the remaining variables $R^3$, n and Y have the abovementioned meaning, and to compounds of general formula III per se;

to a process for the preparation of compounds of general formula IV

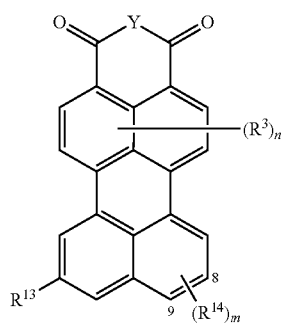

wherein the variables have the following meaning
$R^{13}$, $R^{14}$ independently of each other aryl or hetaryl,
Lg leaving group,
m 0 or 1, where in the case of m equal 1 $R^{14}$ is bound either to the 8 or 9
and the remaining variables $R^3$, n and Y have the abovementioned meaning, and to compounds of general formula IV per se;
to the use of the compounds of general formulae II, III and IV each prepared according to the abovementioned processes and of compounds of general formulae II, III and IV per se for the preparation of dye-sensitized solar cells;
and to such dye-sensitized solar cells per se.

The direct conversion of solar energy to electrical energy in solar cells is based on the internal photoeffect of a semiconductor material, i.e. the generation of electron-hole pairs by absorption of photons and the separation of the negative and positive charge carriers at a p-n junction or a Schottky contact. The photovoltage thus generated can bring about a photocurrent in an external circuit, through which the solar cell delivers its power.

Thin layers or films of metal oxides are known to constitute inexpensive solid semiconductor materials (n-semiconductors), but their absorption, owing to large band gaps, is typically not within the visible region of the electromagnetic spectrum. For use in solar cells, the metal oxides therefore have to be combined with a photosensitizer which absorbs in the wavelength range of sunlight, i.e. at from 300 to 2000 nm, and, in the electronically excited state, injects electrons into the conduction band of the semiconductor. With the aid of a redox system which is used additionally in the cell and is reduced at the counterelectrode, electrons are recycled to the sensitizer which is thus regenerated.

Of particular interest for use in solar cells are the semiconductors zinc oxide, tin dioxide and especially titanium dioxide, which are used in the form of nanocrystalline porous layers. These layers have a large surface area which is coated with the sensitizer, so that high absorption of sunlight is achieved.

Dye-sensitized solar cells (DSCs) which are based on titanium dioxide as the semiconductor material are described, for example, in U.S. Pat. No. 4,927,721, Nature 353, p. 737-740 (1991) and U.S. Pat. No. 5,350,644, and also Nature 395, p. 583-585 (1998) and EP-A-1 176 646. These solar cells comprise monomolecular films of transition metal complexes, especially ruthenium complexes, which are bonded to the titanium dioxide layer via acid groups, as sensitizers and iodine/iodide redox systems present in dissolved form or amorphous organic p-conductors based on spirobifluorenes.

Ruthenium complexes as molecular sensitizers have shown impressive solar-to-electric power conversion efficiencies (PCE) in liquid electrolyte based devices, with the PCE reaching over 11% under standard AM1.5G full sunlight as was shown by M. K. Nazeeruddin, F. De Angelis, S. Fantacci, A. Selloni, G. Viscardi, P. Liska, S. Ito, T. Bessho, M. Grätzel, J. Am. Chem. Soc. 2005, 127, 16835;

Y. Chiba, A. Islam, Y. Watanabe, R. Komiya, N. Koide, L. Y. Han, Jpn. J. Appl. Phys. 2006, 45, L638;

F. Gao, Y. Wang, D. Shi, J. Zhang, M. K. Wang, X. Y. Jing, R. Humphry-Baker, P. Wang, S. M. Zakeeruddin, M. Grätzel, J. Am. Chem. Soc. 2008, 130, 10720;

Y. M. Cao, Y. Bai, Q. J. Yu, Y. M. Cheng, S. Liu, D. Shi, F. Gao, P. Wang, J. Phys. Chem. C 2009, 113, 6290;

and

C.-Y. Chen, M. K. Wang, J.-Y. Li, N. Pootrakulchote, L. Alibabaei, C. H. Ngoc-le, J. D. Decoppet, J. H. Tsai, C. Gratzel, C. G. Wu, S. M. Zakeeruddin, M. Grätzel, ACS Nano 2009, 3, 3103.

In recent years, metal-free organic dyes have attracted increasing attention as they do not contain any toxic or costly metal and their properties are easily tuned by facile structural modification. In addition, they generally have much higher extinction coefficients when compared to Ru(II) polypyridyls, making them excellent for use in solid state DSCs in combination with hole transporting materials such as P3HT as shown, for example, by G. K. Mor, S. Kim, M. Paulose, O. K. Varghese, K. Shankar, J. Basham and C. A. Grimes, Nano Lett., 2009, 9, 4250, or spiro-MeOTAD as shown, for example, by H. J. Snaith, A. J. Moule, C. Klein, K. Meerholz, R. H. Friend, M. Grätzel, Nano Lett., 2007, 7, 3372.

Due to their high extinction coefficients and long-term stability against the action of oxygen and/or light rylene derivatives have attracted much attention as possible sensitizers for DSCs.

Thus, perylene-3,4:9,10-tetracarboxylic acid derivatives as sensitizers are examined in Japanese documents JP-A-10-189065, 2000-243463, 2001-093589, 2000-100484 and 10-334954, and in New J. Chem. 26, p. 1155-1160 (2002).

Further rylene derivatives useful as sensitizers in DSCs are prepared and evaluated in WO 2007/054470 A1.

In order to facilitate tailor-made adjustments of the molecular properties of rylenes, versatile substitution patterns are desirable. To date most rylene derivatives exhibit substitution patterns on bay (1, 6, 7 and/or 12) and/or peri (3, 4, 9 and/or 10) positions as exemplified for the perylene skeleton:

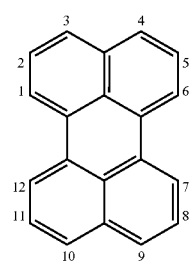

Examples of rylene compounds substituted on the edge (2, 5, 8 and/or 11) position are still scarce.

Direct borylation of perylene in the 2,5,8,11-position is described by D. N. Coventry, A. S. Batsanov, A E. Goeta, J. A. K. Howard, T. B. Marder and R. N. Perutz (Chem. Commun., 2005, 2172-2174).

T. Teraoka, S. Hiroto and H. Shinokubo (Org. Lett. 2011, Vol. 13, No. 10, 2532-2535) and G. Battagliarin, C. Li, V. Enkelmann and K. Mullen (Org. Lett. 2011, Vol. 13, No. 12, 3012-3015) describe the preparation of the 2,5,8,11-tetraboronic ester perylenediimides

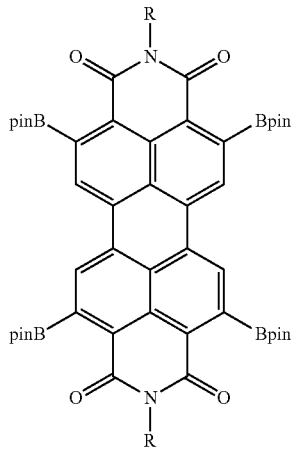

by reacting an unsubstituted perylenediimide in the presence of an iridium or ruthenium catalyst, respectively, and bis(pinacolato)diboron, where Bpin/pinB stand for 4,4,5,5-tetramethyl-1,3,2-dioxaborolan-2-yl substituents and R for hydrocarbon moieties.

2,5,8,11-tetrachloro, -tetrabromo and -tetracyano substituted perylenediimides and their preparation by reacting an unsubstituted perylenediimide with copper dichloride, copper dibromide and copper dicyanide, respectively, are disclosed by G. Battagliarin, Y. Zhao, C. Li and K. Mullen (Org. Lett. 2011, Vol. 13, No. 10, 3399-3401).

Yet rylene 3,4-dicarboximide (perylene monoimide—PMI) derivatives which can be easily substituted on the edge (8 and/or 11) positions of the carbon skeleton are hitherto unknown.

In view of the aforesaid it is the main object of the present invention to provide further convenient building blocks for the preparation of 8- and/or 11-substituted PMIs and 8- and/or 11-substituted PMIs per se for the application in DSCs which exhibit good to very good quantum efficiencies and very good medium to long term stabilities.

Accordingly, compounds of general formula I

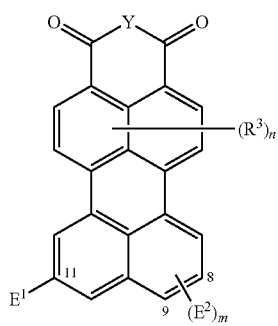 (I)

have been synthesized, wherein the variables have the following meaning
$E^1$, $E^2$ a moiety of formula Ia

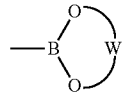 (Ia)

m 0 or 1, where in the case of m equal 1 $E^2$ is bound either to the 8 or 9 position of the perylene skeleton and is identical to $E^1$, W a bridging $C_2$ or $C_3$ moiety which may be substituted by one or more alkyl, $R^3$ identical or different radicals hydrogen, alkyl, cycloalkyl, aryl, hetaryl, alkoxy, aryloxy, arylthio, hetaryloxy, hetarylthio, diarylamino or dialkylamino, n 0, 1, 2, 3 or 4

Y oxygen or $NR^{12}$,
and $R^{12}$ hydrogen, alkyl, cycloalkyl, aryl or hetaryl,
or
a moiety of formula —Z-A, wherein
A is —COOM, —$SO_3$M or —$PO_3$M,
M hydrogen, alkali metal cation or $[NR']^{4+}$,
R' hydrogen or alkyl, where the radicals R' may be identical or different, and
Z $C_1$-$C_6$-alkylene or 1,4-phenylene, where the phenylene radical may be substituted by one or more substituents alkyl, nitro, cyano and/or halogen.

Preferred compounds of general formula I are those wherein the variables have the following meaning
$E^1$, $E^2$ a moiety selected from the group consisting of

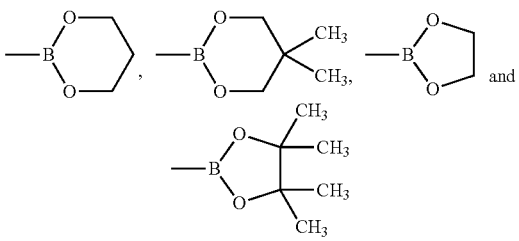

and the remaining variables m, $R^3$, n and Y have the aforementioned meaning according to general formula I.

Specifically preferred compounds are those wherein in general formula I the variables have the following meaning
$E^1$, $E^2$ a moiety selected from the group consisting of

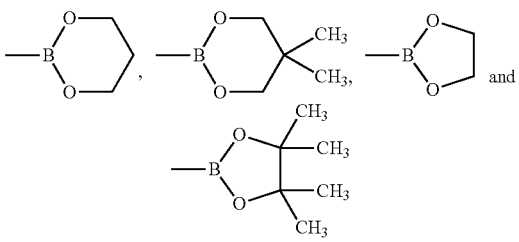

m 0 or 1, where in the case of m equal 1 $E^2$ is bound either to the 8 or 9 position of the perylene skeleton and is identical to $E^1$, R³ identical or different radicals hydrogen, alkyl, cycloalkyl, aryl, alkoxy, aryloxy, diarylamino or dialkylamino,
n 0, 1, 2, 3 or 4
Y oxygen or NR¹²,
R¹² alkyl,
  or
  a moiety of formula —Z-A, wherein
  A is —COOM,
  M hydrogen, alkali metal cation or [NR']⁴⁺,
  R' hydrogen or alkyl, where the radicals R' may be identical or different and
  Z is C₁-C₆-alkylene or 1,4-phenylene.

The aforementioned compounds of general formula I and their preferred embodiments are especially suited as building blocks for the preparation of 8,11- or 9,11-substituted perylene monoimides.

A further objective of the instant invention is a process for the preparation of compounds of general formula I which comprises
reacting a compound of general formula I*

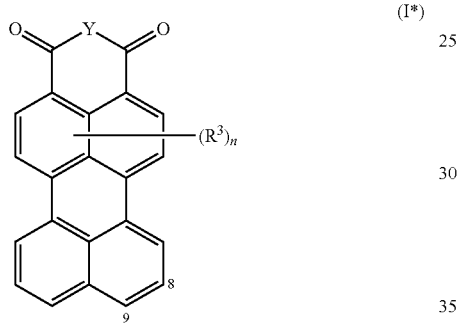

with a compound of general formula Ia*

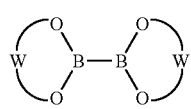

in the presence of bis(1,5-cyclooctadiene)dimethoxydiiridium ([Ir(OCH₃)COD]₂) and 4,4'-di-tert-butyl-2,2'-bipyridyl (dtbpy) in an inert solvent at ambient pressure and temperatures between 20° C. and the boiling point or the inert solvent at ambient pressure,
wherein the variables have the following meaning
W a bridging C₂ or C₃ moiety which may be substituted by one or more alkyl,
R³ identical or different radicals hydrogen, alkyl, cycloalkyl, aryl, hetaryl, alkoxy, aryloxy, arylthio, hetaryloxy, hetarylthio, diarylamino or dialkylamino,
n 0, 1, 2, 3 or 4
Y oxygen or NR¹²,
  and
R¹² hydrogen, alkyl, cycloalkyl, aryl or hetaryl,
  or
  a moiety of formula —Z-A, wherein
  A is —COOM, —SO₃M or —PO₃M,
  M hydrogen, alkali metal cation or [NR']⁴⁺,
  R' hydrogen or alkyl, where the radicals R' may be identical or different, and Z C₁-C₆-alkylene or 1,4-phenylene, where the phenylene radical may be substituted by one or more substituents alkyl, nitro, cyano and/or halogen.

A preferred process for the preparation of compounds of general formula I according to the instant invention comprises
reacting a compound of general formula I*

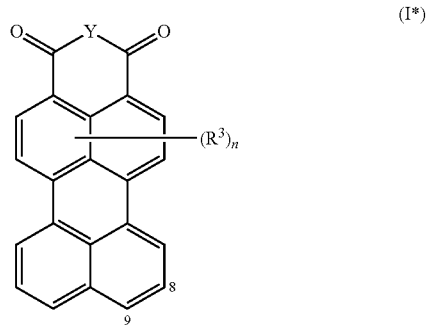

with a compound of general formula Ia* selected from the group consisting of

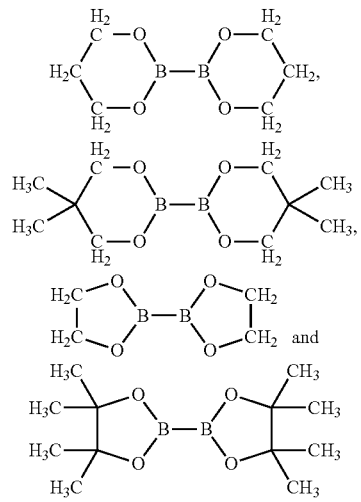

in the presence of bis(1,5-cyclooctadiene)dimethoxydiiridium ([Ir(OCH₃)COD]₂) and 4,4'-di-tert-butyl-2,2'-bipyridyl (dtbpy) in an inert solvent at ambient pressure and temperatures between 20° C. and the boiling point or the inert solvent at ambient pressure,
wherein the variables have the following meaning
R³ identical or different radicals hydrogen, alkyl, cycloalkyl, aryl, hetaryl, alkoxy, aryloxy, arylthio, hetaryloxy, hetarylthio, diarylamino or dialkylamino,
n 0, 1, 2, 3 or 4
Y oxygen or NR¹²,
  and
R¹² hydrogen, alkyl, cycloalkyl, aryl or hetaryl,
  or
  a moiety of formula —Z-A, wherein
  A is —COOM, —SO₃M or —PO₃M,
  M hydrogen, alkali metal cation or [NR']⁴⁺,
  R' hydrogen or alkyl, where the radicals R' may be identical or different, and Z $C_1$-$C_6$-alkylene or 1,4-phenylene, where the phenylene radical may be substituted by one or more substituents alkyl, nitro, cyano and/or halogen.

A specifically preferred process for the preparation of compounds of general formula I according to the instant invention comprises reacting a compound of general formula I*

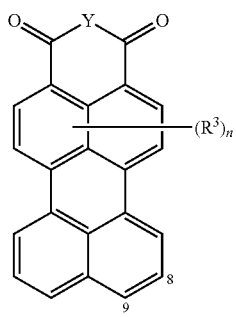

(I*)

with a compound of general formula Ia* selected from the group consisting of

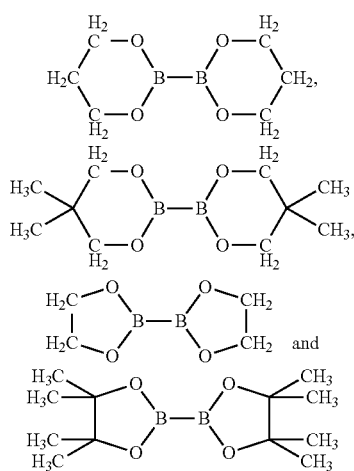

in the presence of bis(1,5-cyclooctadiene)dimethoxydiiridium ([Ir(OCH$_3$)COD]$_2$) and 4,4'-di-tert-butyl-2,2'-bipyridyl (dtbpy) in an inert solvent at ambient pressure and temperatures between 20° C. and the boiling point or the inert solvent at ambient pressure, wherein the variables have the following meaning m 0 or 1, where in the case of m equal 1 $E^2$ is bound either to the 8 or 9 position of the perylene skeleton and is identical to $E^1$, $R^3$ identical or different radicals hydrogen, alkyl, cycloalkyl, aryl, alkoxy, aryloxy, diarylamino or dialkylamino, n 0, 1, 2, 3 or 4

Y oxygen or $NR^{12}$, $R^{12}$ alkyl, or a moiety of formula —Z-A, wherein

A is —COOM,

M hydrogen, alkali metal cation or $[NR']^{4+}$,

R' hydrogen or alkyl, where the radicals R' may be identical or different and

Z is $C_1$-$C_6$-alkylene or 1,4-phenylene.

The term "ambient pressure" denotes basically unconfined reaction conditions, however, not excluding the application of protective gas atmosphere in order to avoid adverse effects by oxygen/air and/or moisture.

"Inert solvent" means a solvent which does not contain moieties with either basic or acidic properties. Especially groups with acidic hydrogen atoms must not be present. In the case of a aromatic or heteroaromatic solvent this may only contain less than three neighboring hydrogen atoms directly bound to the carbon atoms or heteroatoms of the aromatic or heteroaromatic solvent skeleton in order to prevent the aromatic or heteroaromtic solvent from reacting with the boron containing educt. The term "inert solvent" is meant to embrace mixtures of inert solvents as well.

Suitable inert solvents are e.g. dimethyl formamide (DMF), tetrahydrofuran (THF), 1,4-dioxan, octane, hexane, pentane, mesitylene, pinacolone etc. and mixtures thereof.

Further reaction conditions can easily be taken from D. N. Coventry, A. S. Batsanov, A. E. Goeta, J. A. K. Howard, T. B. Marder and R. N. Perutz, Chem. Commun., 2005, 2172-2174.

A further objective of the instant invention is to provide a process for the preparation of compounds of general formula II

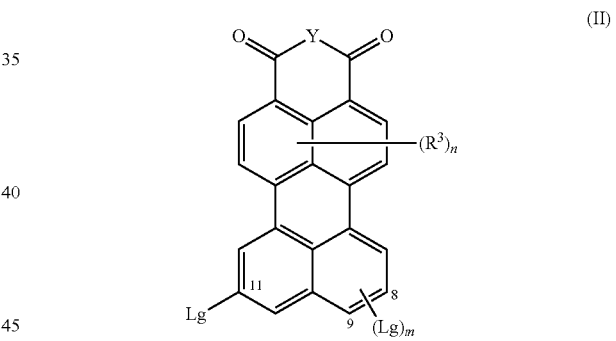

(II)

wherein the variables have the following meaning

Lg leaving group, m 0 or 1, where in the case of m equal 1 the one Lg is bound either to the 8 or 9 position of the perylene skeleton and is identical to the Lg bound to the 11 position, and the remaining variables $R^3$, n and Y have the meaning according to general formula I shown above and preferred embodiments thereof, which comprises reacting a compound of general formula I or preferred embodiments thereof as described above or reacting a compound prepared according to the aforementioned process or preferred embodiments of said process with a compound Cu(Lg)$_2$ in the presence of a polar solvent under confined conditions and temperatures between 20° C. and 140° C.

A preferred process according to the instant invention for the preparation of compounds of general formula II

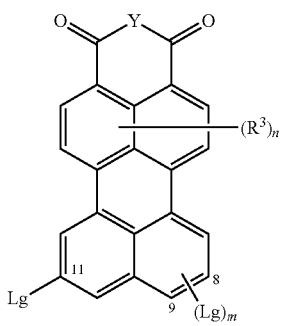

(II)

comprises reacting a compound of general formula I or preferred embodiments thereof as described above or reacting a compound prepared according to the aforementioned process or preferred embodiments of said process with a compound Cu(Lg)$_2$ in the presence of a polar solvent under confined conditions and temperatures between 20° C. and 140° C., wherein the variables have the following meaning Lg chlorine, bromine, iodine, brosylate, nosylate, tosylate, mesylate or triflate, m 0 or 1, where in the case of m equal 1 the one Lg is bound either to the 8 or 9 position of the perylene skeleton and is identical to the Lg bound to the 11 position, and the remaining variables R$^3$, n and Y have the meaning according to the compounds of general formula I described above and preferred embodiments thereof.

The term "confined conditions" refers to reaction conditions in which the reactants during the reaction are placed in a tightly sealed reaction vessel, ampoule or the like.

"Polar solvent" typically refers to a solvent which is readily miscible with water. The term "polar solvent" is meant to embrace mixtures of polar solvents as well. Suitable polar solvents are e.g. water, dimethyl formamide (DMF), tetrahydrofuran (THF), 1,4-dioxan, short carbon chain alcohols like e.g. butanol, i-butanol, tert.-butanol, propanol, i-propanol, ethanol or methanol and mixtures thereof.

In general, the leaving group Lg can be any group known to a person skilled in the art as being prone to easily leave the molecule. Typically, Lg consists of or comprises strongly electron-withdrawing atoms or moieties and, thus, is normally split off as anionic species.

Preferred groups Lg are chlorine, bromine, iodine, brosylate, nosylate, tosylate, mesylate and triflate which, in view of the aforesaid, leave the molecule as chloride, bromide, iodide, brosylate, nosylate, tosylate, mesylate ("mes"—H$_3$C—SO$_3$) or triflate ("tri"—F$_3$C—SO$_3$) anion.

The structure of the brosylate ("bros"), nosylate ("nos") and tosylate ("tos") are, in respective order, as follows:

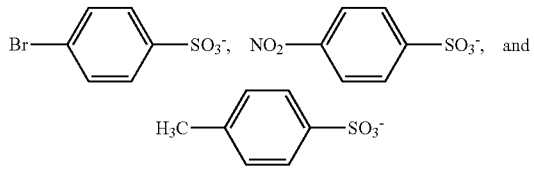

Accordingly, preferred reagents Cu(Lg)$_2$ are CuCl$_2$, CuBr$_2$, CuI$_2$, Cu(bros)$_2$, Cu(nos)$_2$, Cu(tos)$_2$, Cu(mes)$_2$ and Cu(tri)$_2$.

Further reaction conditions can easily be taken from G. Battagliarin, Y. Zhao, C. Li and K. Mullen (Org. Lett. 2011, Vol. 13, No. 10, 3399-3401) and the respective references cited therein.

A further objective of the instant invention are compounds of general formula II

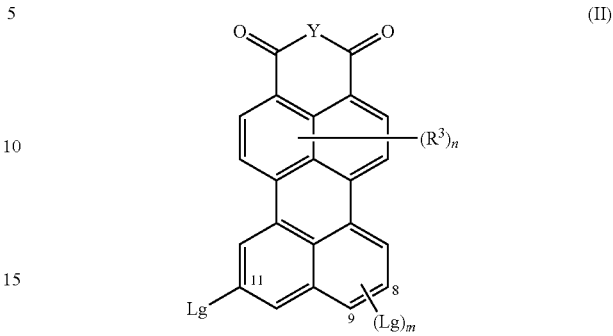

(II)

wherein the variables have the following meaning

Lg leaving group, m 0 or 1, where in the case of m equal 1 the one Lg is bound either to the 8 or 9 position of the perylene skeleton and is identical to the Lg bound to the 11 position, R$^3$ identical or different radicals hydrogen, alkyl, cycloalkyl, aryl, hetaryl, alkoxy, aryloxy, arylthio, hetaryloxy, hetarylthio, diarylamino or dialkylamino, n 0, 1, 2, 3 or 4

Y oxygen or NR$^{12}$, and

R$^{12}$ hydrogen, alkyl, cycloalkyl, aryl or hetaryl, or a moiety of formula —Z-A, wherein A is —COOM, —SO$_3$M or —PO$_3$M, M hydrogen, alkali metal cation or [NR']$^{4+}$, R' hydrogen or alkyl, where the radicals R' may be identical or different, and Z C$_1$-C$_6$-alkylene or 1,4-phenylene, where the phenylene radical may be substituted by one or more substituents alkyl, nitro, cyano and/or halogen.

Preferred compounds according to the instant invention are of general formula II

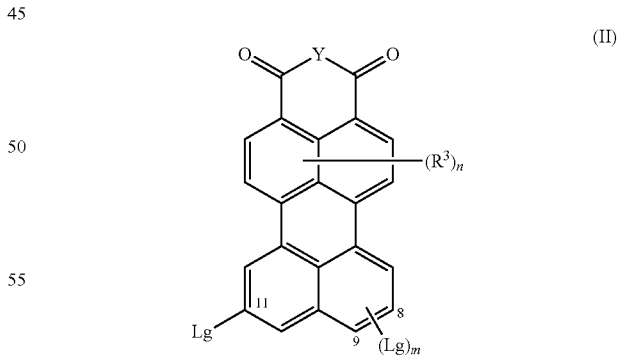

(II)

wherein the variables have the following meaning

Lg chlorine, bromine, iodine, brosylate, nosylate, tosylate, mesylate or triflate, m 0 or 1, where in the case of m equal 1 the one Lg is bound either to the 8 or 9 position of the perylene skeleton and is identical to the Lg bound to the 11 position, R$^3$ identical or different radicals hydrogen, alkyl, cycloalkyl, aryl, alkoxy, aryloxy, diarylamino or dialkylamino, n 0, 1, 2, 3 or 4

Y oxygen or $NR^{12}$, $R^{12}$ alkyl, or a moiety of formula —Z-A, wherein

A is —COOM,

M hydrogen, alkali metal cation or $[NR']^{4+}$,

R' hydrogen or alkyl, where the radicals R' may be identical or different, and

Z $C_1$-$C_6$-alkylene or 1,4-phenylene.

A further objective of the instant invention is a process for the preparation of compounds of general formula III

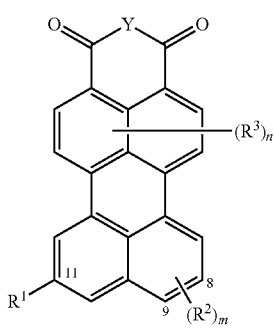
(III)

wherein the variables have the following meaning $R^1$, $R^2$ independently of each other a moiety of formula IIIa

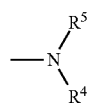
(IIIa)

$R^4$, $R^5$ independently of each other aryl or hetaryl, m 0 or 1, where in the case of m equal 1 $R^2$ is bound either to the 8 or 9 position of the perylene skeleton, and the remaining variables $R^3$, n and Y have the aforementioned meaning according to general formula II and its preferred embodiment comprising reacting a compound of general formula II or its preferred embodiment with a compound or a mixture of compounds of general formula IIIa*

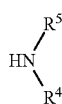
(IIIa*)

in the presence of a palladium containing catalyst under the conditions of the Buchwald-Hartwig amination reaction.

In a preferred process according to the instant invention for the preparation of compounds of general formula III the variables have the following meaning $R^1$, $R^2$ independently of each other halogen or a moiety of formula Ia

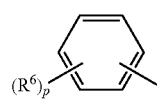
(Ia)

m 0 or 1, where in the case of m equal 1 $R^2$ is bound either to the 8 or 9 position of the perylene skeleton, $R^4$, $R^5$ independently of each other moieties of formulae Ib or Ic

(Ib)

(Ic)

$R^6$ hydrogen, alkyl, aryl, alkoxy, alkylthio or —$NR^7R^8$, where in case of two or more substituents (p equal or greater than 2) these may be identical or different, p 0, 1, 2, 3, 4 or 5, X $C(R^9R^{10})_2$, $NR^{11}$, oxygen or sulfur, $R^7$ to $R^{11}$ hydrogen, alkyl, cycloalkyl, aryl or hetaryl, and the remaining variables $R^3$, n and Y have the aforementioned meaning according to general formula II and its preferred embodiment.

The Buchwald-Hartwig amination reaction is a well established synthetic route and the reaction conditions can easily be determined by a person skilled in the art. Conversion of aryl bromides to arylamines is specifically addressed in the publication by Guram, A. S.; Rennels, R. A.; Buchwald, S. L. (1995), "A Simple Catalytic Method for the Conversion of Aryl Bromides to Arylamines", Angewandte Chemie International Edition 34 (12): 1348-1350.

A further objective of the instant invention are compounds of general formula III

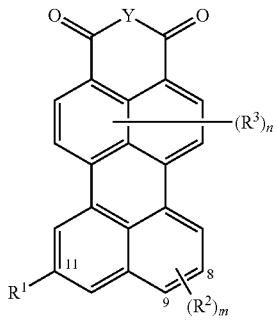
(III)

wherein the variables have the following meaning
$R^1$, $R^2$ independently of each other a moiety of formula IIIa

(IIIa)

$R^4$, $R^5$ independently of each other aryl or hetaryl,
m 0 or 1, where in the case of m equal 1 the respective $R^2$ is bound either to the 8 or 9 position of the perylene skeleton,
$R^3$ identical or different radicals hydrogen, alkyl, cycloalkyl, aryl, hetaryl, alkoxy, aryloxy, arylthio, hetaryloxy, hetarylthio, diarylamino or dialkylamino,
n 0, 1, 2, 3 or 4
Y oxygen or $NR^{12}$,
and
$R^{12}$ hydrogen, alkyl, cycloalkyl, aryl or hetaryl,
or
a moiety of formula —Z-A, wherein
A is —COOM, —$SO_3M$ or —$PO_3M$,
M hydrogen, alkali metal cation or $[NR']^{4+}$,
R' hydrogen or alkyl, where the radicals R' may be identical or different,
and
Z $C_1$-$C_6$-alkylene or 1,4-phenylene, where the phenylene radical may be substituted by one or more substituents alkyl, nitro, cyano and/or halogen.
Preferred compounds of general formula III

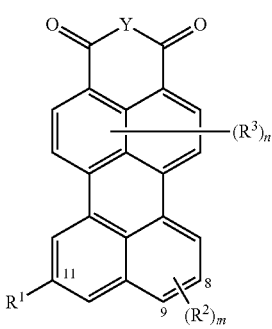
(III)

are those in which the variables have the following meaning
$R^1$, $R^2$ independently of each other a moiety of formula IIIa

(IIIa)

$R^4$, $R^5$ independently of each other aryl or hetaryl,
m 0 or 1, where in the case of m equal 1 the respective $R^2$ is bound either to the 8 or 9 position of the perylene skeleton,
$R^3$ identical or different radicals hydrogen, alkyl, cycloalkyl, aryl, alkoxy, aryloxy, diarylamino or dialkylamino,
n 0, 1, 2, 3 or 4
Y oxygen or $NR^{12}$,
$R^{12}$ alkyl,
or
a moiety of formula —Z-A, wherein A is —COOM,
M hydrogen, alkali metal cation or $[NR']^{4+}$,
R' hydrogen or alkyl, where the radicals R' may be identical or different,
and
Z $C_1$-$C_6$-alkylene or 1,4-phenylene.
Further preferred compounds of general formula III

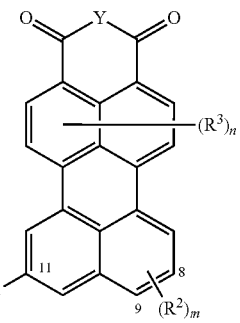
(III)

are those in which the variables have the following meaning
$R^1$, $R^2$ independently of each other halogen or a moiety of formula Ia

(Ia)

m 0 or 1, where in the case of m equal 1 $R^2$ is bound either to the 8 or 9 position of the perylene skeleton,
$R^4$, $R^5$ independently of each other moieties of formulae Ib or Ic

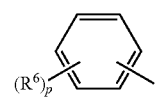
(Ib)

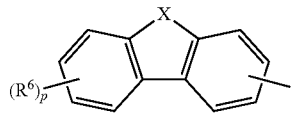
(Ic)

$R^6$ hydrogen, alkyl, aryl, alkoxy, alkylthio or —$NR^7R^6$, where in case of two or more substituents (p equal or greater than 2) these may be identical or different,
p 0, 1, 2, 3, 4 or 5,
X $C(R^9R^{10})_2$, $NR^{11}$, oxygen or sulfur,
$R^7$ to $R^{11}$ hydrogen, alkyl, cycloalkyl, aryl or hetaryl,
$R^3$ identical or different radicals hydrogen, alkyl, cycloalkyl, aryl, hetaryl, alkoxy, aryloxy, arylthio, hetaryloxy, hetarylthio, diarylamino or dialkylamino,
n 0, 1, 2, 3 or 4
Y oxygen or $NR^{12}$,
and
$R^{12}$ hydrogen, alkyl, cycloalkyl, aryl or hetaryl,
or
a moiety of formula —Z-A, wherein
A is —COOM, —$SO_3M$ or —$PO_3M$, M hydrogen, alkali metal cation or $[NR']^{4+}$,
R' hydrogen or alkyl, where the radicals R' may be identical or different,
and
Z $C_1$-$C_8$-alkylene or 1,4-phenylene, where the phenylene radical may be substituted by one or more substituents alkyl, nitro, cyano and/or halogen.

Further preferred compounds of general formula III

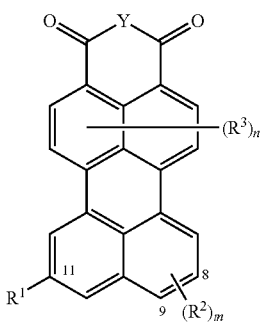

are those in which the variables have the following meaning
$R^1$, $R^2$ independently of each other halogen or a moiety of formula Ia

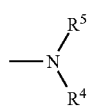

m 0 or 1, where in the case of m equal 1 $R^2$ is bound either to the 8 or 9 position of the perylene skeleton,
$R^4$, $R^5$ independently of each other moieties of formulae Ib or Ic

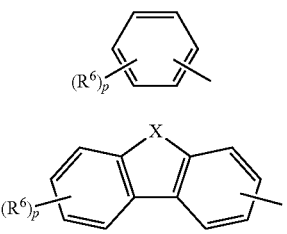

$R^6$ hydrogen, alkyl, aryl, alkoxy, alkylthio or —$NR^7R^6$, where in case of two or more substituents (p equal or greater than 2) these may be identical or different,
p 0, 1, 2, 3, 4 or 5,
X $C(R^9R^{10})_2$, $NR^{11}$, oxygen or sulfur,
$R^7$ to $R^{11}$ hydrogen, alkyl, cycloalkyl, aryl or hetaryl,
$R^3$ identical or different radicals hydrogen, alkyl, cycloalkyl, aryl, alkoxy, aryloxy, diarylamino or dialkylamino,
n 0, 1, 2, 3 or 4
Y oxygen or $NR^{12}$,
$R^{12}$ alkyl,
or
a moiety of formula —Z-A, wherein
A is —COOM,
M hydrogen, alkali metal cation or $[NR']^{4+}$,
R' hydrogen or alkyl, where the radicals R' may be identical or different,
and
Z $C_1$-$C_6$-alkylene or 1,4-phenylene.

A further objective of the instant invention is a process for the preparation of compounds of general formula IV

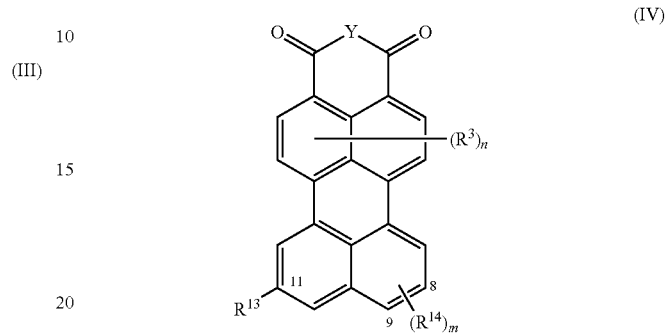

wherein the variables have the following meaning
$R^{13}$, $R^{14}$ independently of each other aryl or hetaryl,
Lg leaving group,
m 0 or 1, where in the case of m equal 1 $R^{14}$ is bound either to the 8 or 9 position of the perylene skeleton,
and the remaining variables $R^3$, n and Y have the meaning according to general formula I and its preferred embodiments,
which comprises reacting a compound of general formula I or preferred embodiments of such compounds with compounds of general formula Lg-$R^{13}$ and Lg-$R^{14}$ in the presence of a palladium containing catalyst under the conditions of the Suzuki coupling reaction.

In a preferred embodiment of the aforementioned process the variables in general formula IV have the following meaning
$R^{13}$, $R^{14}$ independently of each other moieties of formulae IVa or IVb

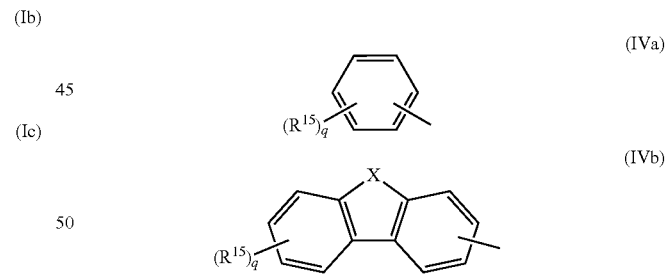

$R^{15}$ hydrogen, alkyl, aryl, alkoxy, alkylthio or —$NR^{16}R^{17}$, where in case of two or more substituents (q equal or greater than 2) these may be identical or different,
q 0, 1, 2, 3, 4 or 5,
X $C(R^{18}R^{19})_2$, $NR^{20}$, oxygen or sulfur,
$R^{16}$ to $R^{20}$ hydrogen, alkyl, aryl or hetaryl,
m 0 or 1, where in the case of m equal 1 $R^{14}$ is bound either to the 8 or 9 position of the perylene skeleton,
and the remaining variables $R^3$, n and Y have the meaning according to general formula I and the preferred embodiments thereof.

In a specifically preferred process—also with reference to its aforementioned preferred embodiments—the variables Lg of Lg-$R^{13}$ and Lg-$R^{14}$ have the following meaning Lg chlorine, bromine, iodine, brosylate, nosylate, tosylate, mesylate or triflate, and the remaining variables have the aforementioned meaning with respect to the preferred embodiments.

A further objective of the instant invention are compounds of general formula IV

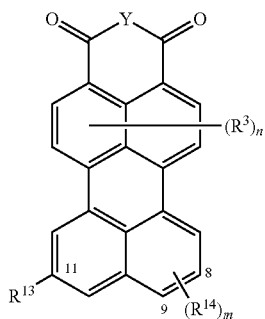

(IV)

wherein the variables have the following meaning $R^{13}$, $R^{14}$ independently of each other aryl or hetaryl, m 0 or 1, where in the case of m equal 1 $R^{14}$ is bound either to the 8 or 9 position of the perylene skeleton and is identical to $R^{13}$, $R^3$ identical or different radicals hydrogen, alkyl, cycloalkyl, aryl, hetaryl, alkoxy, aryloxy, arylthio, hetaryloxy, hetarylthio, diarylamino or dialkylamino, n 0, 1, 2, 3 or 4

Y oxygen or $NR^{12}$, and $R^{12}$ hydrogen, alkyl, cycloalkyl, aryl or hetaryl, or a moiety of formula —Z-A, wherein A is —COOM, —SO$_3$M or —PO$_3$M, M hydrogen, alkali metal cation or $[NR']^{4+}$, R' hydrogen or alkyl, where the radicals R' may be identical or different, and Z $C_1$-$C_6$-alkylene or 1,4-phenylene, where the phenylene radical may be substituted by one or more substituents alkyl, nitro, cyano and/or halogen.

A further objective of the instant invention are compounds of general formula IV

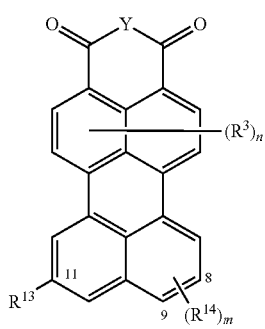

(IV)

wherein the variables have the following meaning $R^{13}$, $R^{14}$ independently of each other aryl or hetaryl, m 0 or 1, where in the case of m equal 1 $R^{14}$ is bound either to the 8 or 9 position of the perylene skeleton and is identical to $R^{13}$, $R^3$ identical or different radicals hydrogen, alkyl, cycloalkyl, aryl, hetaryl, alkoxy, aryloxy, arylthio, hetaryloxy, hetarylthio, diarylamino or dialkylamino, n 0, 1, 2, 3 or 4

Y oxygen or $NR^{12}$, and $R^{12}$ hydrogen, alkyl, cycloalkyl, aryl or hetaryl, or a moiety of formula —Z-A, wherein A is —COOM, —SO$_3$M or —PO$_3$M, M hydrogen, alkali metal cation or $[NR']^{4+}$, R' hydrogen or alkyl, where the radicals R' may be identical or different, and Z $C_1$-$C_6$-alkylene or 1,4-phenylene, where the phenylene radical may be substituted by one or more substituents alkyl, nitro, cyano and/or halogen.

Preferred compounds of general formula IV

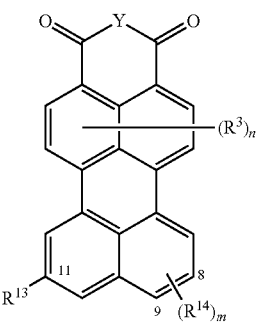

(IV)

are those in which the variables have the following meaning $R^{13}$, $R^{14}$ independently of each other aryl or hetaryl, m 0 or 1, where in the case of m equal 1 $R^{14}$ is bound either to the 8 or 9 position of the perylene skeleton and is identical to $R^{13}$, $R^3$ identical or different radicals hydrogen, alkyl, cycloalkyl, aryl, alkoxy, aryloxy, diarylamino or dialkylamino, n 0, 1, 2, 3 or 4

Y oxygen or $NR^{12}$, and $R^{12}$ alkyl, or a moiety of formula —Z-A, wherein

A is —COOM,

M hydrogen, alkali metal cation or $[NR']^{4+}$,

R' hydrogen or alkyl, where the radicals R' may be identical or different,

Z $C_1$-$C_6$-alkylene or 1,4-phenylene.

Further preferred compounds of general formula IV

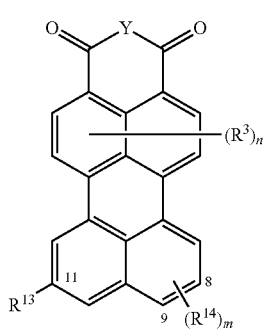

(IV)

are those in which the variables have the following meaning
$R^{13}$, $R^{14}$ independently of each other moieties of formulae IVa or IVb

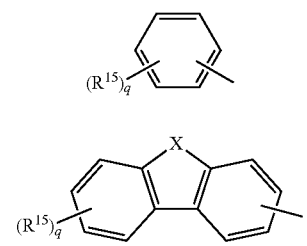

(IVa)

(IVb)

$R^{15}$ hydrogen, alkyl, aryl, alkoxy, alkylthio or —$NR^{16}R^{17}$, where in case of two or more substituents (q equal or greater than 2) these may be identical or different, q 0, 1, 2, 3, 4 or 5, X $C(R^{16}R^{19})_2$, $NR^{20}$, oxygen or sulfur, $R^{16}$ to $R^{20}$ hydrogen, alkyl, aryl or hetaryl, m 0 or 1, where in the case of m equal 1 $R^{14}$ is bound either to the 8 or 9 position of the perylene skeleton and is identical to $R^{13}$, $R^3$ identical or different radicals hydrogen, alkyl, cycloalkyl, aryl, hetaryl, alkoxy, aryloxy, arylthio, hetaryloxy, hetarylthio, diarylamino or dialkylamino, n 0, 1, 2, 3 or 4

Y oxygen or $NR^{12}$,
and $R^{12}$ hydrogen, alkyl, cycloalkyl, aryl or hetaryl,
or
a moiety of formula —Z-A, wherein
A is —COOM, —$SO_3M$ or —$PO_3M$,
M hydrogen, alkali metal cation or $[NR']^{4+}$,
R' hydrogen or alkyl, where the radicals R' may be identical or different,
and
Z $C_1$-$C_6$-alkylene or 1,4-phenylene, where the phenylene radical may be substituted by one or more substituents alkyl, nitro, cyano and/or halogen.

Further preferred compounds of general formula IV

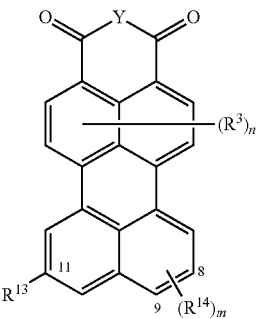

(IV)

are those in which the variables have the following meaning
$R^{13}$, $R^{14}$ independently of each other moieties of formulae IVa or IVb (IVa)

(IVb)

$R^{15}$ hydrogen, alkyl, aryl, alkoxy, alkylthio or —$NR^{16}R^{17}$, where in case of two or more substituents (q equal or greater than 2) these may be identical or different, q 0, 1, 2, 3, 4 or 5, X $C(R^{18}R^{16})_2$, $NR^{20}$, oxygen or sulfur, $R^{16}$ to $R^{20}$ hydrogen, alkyl, aryl or hetaryl, m 0 or 1, where in the case of m equal 1 $R^{14}$ is bound either to the 8 or 9 position of the perylene skeleton and is identical to $R^{13}$, $R^3$ identical or different radicals hydrogen, alkyl, cycloalkyl, aryl, alkoxy, aryloxy, diarylamino or dialkylamino, n 0, 1, 2, 3 or 4

Y oxygen or $NR^{12}$,
and
$R^{12}$ alkyl,
or
a moiety of formula —Z-A, wherein
A is —COOM,
M hydrogen, alkali metal cation or $[NR']^{4+}$,
R' hydrogen or alkyl, where the radicals R' may be identical or different,
Z $C_1$-$C_6$-alkylene or 1,4-phenylene.

A further objective or the instant invention is the use
of compounds of general formula II prepared according to abovementioned process and its preferred embodiments,
of compounds of general formula III prepared according to the abovementioned process and its preferred embodiments,
of compounds of general formula IV prepared according to the abovementioned process and its preferred embodiments,
of compounds of general formula II and their preferred abovementioned embodiments, of compounds of claim 12 and their preferred abovementioned embodiments and of compounds of general formula IV and their preferred abovementioned embodiments for the preparation of dye-sensitized solar cells.

A further objective or the instant invention is a dye-sensitized solar cell comprising compounds of general formula III prepared according to the abovementioned process and its preferred embodiments, compounds of general formula IV prepared according to the abovementioned process and its preferred embodiments, compounds of general formula II and their preferred abovementioned embodiments, compounds of claim 12 and their preferred abovementioned embodiments or compounds of general formula IV and their preferred abovementioned embodiments.

In the context of the present invention, alkyl, aryl or heteroaryl represents unsubstituted or substituted alkyl, unsubstituted or substituted aryl or unsubstituted or substituted heteroaryl.

Alkyl comprises straight-chain or branched alkyl. Alkyl is preferably $C_1$-$C_{30}$-alkyl, especially $C_1$-$C_{20}$-alkyl and most preferably $C_1$-$C_{12}$-alkyl. Examples of alkyl groups are especially methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

Further examples of branched alkyl groups can be represented by the following formula

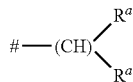

in which # denotes a bonding site, and $R^a$ is selected from $C_1$- to $C_{28}$-alkyl, where the sum of the carbon atoms of the $R^g$ radicals is an integer from 2 to 29.

In the formula above, the $R^a$ radicals are preferably selected from $C_1$- to $C_{12}$-alkyl, especially $C_1$- to $C_8$-alkyl.

Preferred branched alkyl radicals of the above formula are, for example:

1-ethylpropyl, 1-methylpropyl, 1-propylbutyl, 1-ethylbutyl, 1-methylbutyl, 1-butylpentyl, 1-propylpentyl, 1-ethylpentyl, 1-methylpentyl, 1-pentylhexyl, 1-butylhexyl, 1-propylhexyl, 1-ethylhexyl, 1-methylhexyl, 1-hexylheptyl, 1-pentylheptyl, 1-butylheptyl, 1-propylheptyl, 1-ethylheptyl, 1-methylheptyl, 1-heptyloctyl, 1-hexyloctyl, 1-pentyloctyl, 1-butyloctyl, 1-propyloctyl, 1-ethyloctyl, 1-methyloctyl, 1-octylnonyl, 1-heptylnonyl, 1-hexylnonyl, 1-pentylnonyl, 1-butylnonyl, 1-propylnonyl, 1-ethylnonyl, 1-methylnonyl, 1-nonyldecyl, 1-octyldecyl, 1-heptyldecyl, 1-hexyldecyl, 1-pentyldecyl, 1-butyldecyl, 1-propyldecyl, 1-ethyldecyl, 1-methyldecyl, 1-decylundecyl, 1-nonylundecyl, 1-octylundecyl, 1-heptylundecyl, 1-hexylundecyl, 1-pentylundecyl, 1-butylundecyl, 1-propylundecyl, 1-ethylundecyl, 1-methylundecyl, 1-undecyldodecyl, 1-decyldodecyl, 1-nonyldodecyl, 1-octyldodecyl, 1-heptyldodecyl, 1-hexyldodecyl, 1-pentyldodecyl, 1-butyldodecyl, 1-propyldodecyl, 1-ethyldodecyl, 1-methyldodecyl, 1-dodecyltridecyl, 1-undecyltridecyl, 1-decyltridecyl, 1-nonyltridecyl, 1-octyltridecyl, 1-heptyltridecyl, 1-hexyltridecyl, 1-pentyltridecyl, 1-butyltridecyl, 1-propyltridecyl, 1-ethyltridecyl, 1-methyltridecyl, 1-tridecyltetradecyl, 1-undecyltetradecyl, 1-decyltetradecyl, 1-nonyltetradecyl, 1-octyltetradecyl, 1-heptyltetradecyl, 1-hexyltetradecyl, 1-pentyltetradecyl, 1-butyltetradecyl, 1-propyltetradecyl, 1-ethyltetradecyl, 1-methyltetradecyl, 1-pentadecylhexadecyl, 1-tetradecylhexadecyl, 1-tridecylhexadecyl, 1-dodecylhexadecyl, 1-undecylhexadecyl, 1-decylhexadecyl, 1-nonylhexadecyl, 1-octylhexadecyl, 1-heptylhexadecyl, 1-hexylhexadecyl, 1-pentylhexadecyl, 1-butylhexadecyl, 1-propylhexadecyl, 1-ethylhexadecyl, 1-methylhexadecyl, 1-hexadecyloctadecyl, 1-pentadecyloctadecyl, 1-tetradecyloctadecyl, 1-tridecyloctadecyl, 1-dodecyloctadecyl, 1-undecyloctadecyl, 1-decyloctadecyl, 1-nonyloctadecyl, 1-octyloctadecyl, 1-heptyloctadecyl, 1-hexyloctadecyl, 1-pentyloctadecyl, 1-butyloctadecyl, 1-propyloctadecyl, 1-ethyloctadecyl, 1-methyloctadecyl, 1-nonadecyleicosanyl, 1-octadecyleicosanyl, 1-heptadecyleicosanyl, 1-hexadecyleicosanyl, 1-pentadecyleicosanyl, 1-tetradecyleicosanyl, 1-tridecyleicosanyl, 1-dodecyleicosanyl, 1-undecyleicosanyl, 1-decyleicosanyl, 1-nonyleicosanyl, 1-octyleicosanyl, 1-heptyleicosanyl, 1-hexyleicosanyl, 1-pentyleicosanyl, 1-butyleicosanyl, 1-propyleicosanyl, 1-ethyleicosanyl, 1-methyleicosanyl, 1-eicosanyldocosanyl, 1-nonadecyldocosanyl, 1-octadecyldocosanyl, 1-heptadecyldocosanyl, 1-hexadecyldocosanyl, 1-pentadecyldocosanyl, 1-tetradecyldocosanyl, 1-tridecyldocosanyl, 1-undecyldocosanyl, 1-decyldocosanyl, 1-nonyldocosanyl, 1-octyldocosanyl, 1-heptyldocosanyl, 1-hexyldocosanyl, 1-pentyldocosanyl, 1-butyldocosanyl, 1-propyldocosanyl, 1-ethyldocosanyl, 1-methyldocosanyl, 1-tricosanyltetracosanyl, 1-docosanyltetracosanyl, 1-nonadecyltetracosanyl, 1-octadecyltetracosanyl, 1-heptadecyltetracosanyl, 1-hexadecyltetracosanyl, 1-pentadecyltetracosanyl, 1-pentadecyltetracosanyl, 1-tetradecyltetracosanyl, 1-tridecyltetracosanyl, 1-dodecyltetracosanyl, 1-undecyltetracosanyl, 1-decyltetracosanyl, 1-nonyltetracosanyl, 1-octyltetracosanyl, 1-heptyltetracosanyl, 1-hexyltetracosanyl, 1-pentyltetracosanyl, 1-butyltetracosanyl, 1-propyltetracosanyl, 1-ethyltetracosanyl, 1-methyltetracosanyl, 1-heptacosanyloctacosanyl, 1-hexacosanyloctacosanyl, 1-pentacosanyloctacosanyl, 1-tetracosanyloctacosanyl, 1-tricosanyloctacosanyl, 1-docosanyloctacosanyl, 1-nonadecyloctacosanyl, 1-octadecyloctacosanyl, 1-heptadecyloctacosanyl, 1-hexadecyloctacosanyl, 1-pentadecyloctacosanyl, 1-tetradecyloctacosanyl, 1-tridecyloctacosanyl, 1-dodecyloctacosanyl, 1-undecyloctacosanyl, 1-decyloctacosanyl, 1-nonyloctacosanyl, 1-octyloctacosanyl, 1-heptyloctacosanyl, 1-hexyloctacosanyl, 1-pentyloctacosanyl, 1-butyloctacosanyl, 1-propyloctacosanyl, 1-ethyloctacosanyl, 1-methyloctacosanyl.

Alkyl also comprises alkyl radicals whose carbon chains may be interrupted by one or more nonadjacent groups selected from oxygen, sulfur, —CO—, —$NR^b$—, —SO— and/or —$SO_2$— where $R^b$ is preferably hydrogen, unsubstituted straight-chain or branched alkyl as described before or unsubstituted aryl as described below.

Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, hetaryl, fluorine, chlorine, bromine, cyano and nitro.

Aryl-substituted alkyl radicals (aralkyl) have at least one unsubstituted or substituted aryl group, as defined below. The alkyl group of the aralkyl radical may bear at least one further substituent and/or be interrupted by one or more nonadjacent groups selected from oxygen, sulfur, —CO—, —$NR^b$—, —SO— and/or —SO$_2$— where $R^b$ is preferably hydrogen, unsubstituted straight-chain or branched alkyl as described before or unsubstituted aryl as described below. Arylalkyl is preferably phenyl-C$_1$-C$_{10}$-alkyl, more preferably phenyl-C$_1$-C$_4$-alkyl, for example benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl, 4-phenbut-2-yl, 1-(phenmeth)eth-1-yl, 1-(phenmethyl)-1-(methyl)eth-1-yl or -(phenmethyl)-1-(methyl)prop-1-yl; preferably benzyl and 2-phenethyl.

Halogen-substituted alkyl groups (haloalkyl) comprise a straight-chain or branched alkyl group in which at least one hydrogen atom or all hydrogen atoms are replaced by halogen. The halogen atoms are preferably selected from fluorine, chlorine and bromine, especially fluorine and chlorine. Examples of haloalkyl groups are especially chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, —CH$_2$—C$_2$F$_5$, —CF$_2$—C$_2$F$_5$, —CF(CF$_3$)$_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl.

The above remarks regarding unsubstituted or substituted alkyl also apply to unsubstituted or substituted alkoxy and unsubstituted or substituted dialkylamino.

Specific examples of unsubstituted and substituted alkyl radicals which may be interrupted by one or more nonadjacent groups selected from oxygen, sulfur, —NR$^b$—, —CO—, —SO— and/or —SO$_2$— are:

methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl, 2-methoxyethyl, 2-ethoxyethyl, 2-propoxyethyl, 2-butoxyethyl, 3-methoxypropyl, 3-ethoxypropyl, 3-propoxypropyl, 3-butoxypropyl, 4-methoxybutyl, 4-ethoxybutyl, 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetraoxatetradecyl;

2-methylthioethyl, 2-ethylthioethyl, 2-propylthioethyl, 2-butylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfinylethyl, 2-ethylsulfinylethyl, 2-propylsulfinylethyl, 2-isopropylsulfinylethyl, 2-butylsulfinylethyl, 2- and 3-methylsulfinylpropyl, 2- and 3-ethylsulfinylpropyl, 2- and 3-propylsulfinylpropyl, 2- and 3-butylsulfinylpropyl, 2- and 4-methylsulfinylbutyl, 2- and 4-ethylsulfinylbutyl, 2- and 4-propylsulfinylbutyl and 4-butylsulfinylbutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylproypl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxyl-tetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 3- and 4-hydroxybutyl and 8-hydroxyl-4-oxaoctyl;

2-cyanoethyl, 3-cyanopropyl, 3- and 4-cyanobutyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, butoxy, pentoxy and hexoxy;

methylthio, ethylthio, propylthio, butylthio, pentylthio and hexylthio;

methylamino, ethylamino, propylamino, butylamino, pentylamino, hexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butyl-aminocarbonyl, pentylaminocarbonyl, hexylaminocarbonyl, heptylaminocarbonyl, octylaminocarbonyl, nonylaminocarbonyl, decylaminocarbonyl and phenylamino-carbonyl;

aminosulfonyl, n-dodecylaminosulfonyl, N,N-diphenylaminosulfonyl, and N,N-bis(4-chlorophenyl)aminosulfonyl;

methoxycarbonyl, ethoxycarbonyl, propoxycarbonyl hexoxycarbonyl, dodecyloxycarbonyl, octadecyloxycarbonyl, phenoxycarbonyl, (4-tert-butylphenoxy)carbonyl and (4-chlorophenoxy)carbonyl;

methoxysulfonyl, ethoxysulfonyl, propoxysulfonyl, butoxysulfonyl, hexoxysulfonyl, dodecyloxysulfonyl and octadecyloxysulfonyl.

In the context of the invention, cycloalkyl denotes a cycloaliphatic radical having preferably 3 to 10, more preferably 5 to 8, carbon atoms. Examples of cycloalkyl groups are especially cyclopropyl, cyclobutyl, cyclopentyl, cyclohexyl, cycloheptyl or cyclooctyl.

Substituted cycloalkyl groups may, depending on the ring size, have one or more (e.g. 1, 2, 3, 4, 5 or more than 5) substituents. These are preferably each independently selected from alkyl, alkoxy, alkylamino, alkylthio, cycloalkyl, heterocycloalkyl, aryl, hetaryl, fluorine, chlorine, bromine, cyano and nitro. In the case of substitution, the cycloalkyl groups preferably bear one or more, for example one, two, three, four or five, $C_1$-$C_6$-alkyl groups. Examples of substituted cycloalkyl groups are especially 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec.-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methylcyclooctyl, 2-, 3-, 4- and 5-ethylcyclooctyl, 2-, 3-, 4- and 5-propylcyclooctyl.

Specific examples of substituted and unsubstituted cycloalkyl groups are cyclopropyl, cyclobutyl, cyclopentyl, 2- and 3-methylcyclopentyl, 2- and 3-ethylcyclo-pentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methyl-cycloheptyl, 2-, 3- and 4-ethylcycloheptyl, 3- and 4-propylcycloheptyl, 3- and 4-iso-propylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

In the context of the present invention, aryl comprises mono- or polycyclic aromatic hydrocarbon radicals and monocyclic aromatic hydrocarbon radicals which may be fused to one or more unfused or fused saturated or unsaturated carbocyclic or heterocyclic five or six membered rings. Aryl has preferably 6 to 14, more preferably 6 to 10, carbon atoms. Examples of aryl are especially phenyl, naphthyl, indenyl, fluorenyl, anthracenyl, phenanthrenyl, naphthacenyl, chrysenyl and pyrenyl, especially phenyl, naphthyl and fluorenyl.

Substituted aryls may, depending on the number and size of their ring systems, have one or more (e.g. 1, 2, 3, 4, 5 or more than 5) substituents. These are preferably each independently selected from alkyl, alkoxy, alkylamino, alkylthio, cycloalkyl, heterocycloalkyl, aryl, hetaryl, fluorine, chlorine, bromine, cyano and nitro. The alkyl, alkoxy, alkylamino, alkylthio, cycloalkyl, heterocycloalkyl, aryl and hetaryl substituents on the aryl may in turn be unsubstituted or substituted. Reference is made to the substituents mentioned above for these groups. The substituents on the aryl are preferably selected from alkyl, alkoxy, haloalkyl, haloalkoxy, aryl, fluorine, chlorine, bromine, cyano and nitro. Substituted aryl is more preferably substituted phenyl which generally bears 1, 2, 3, 4 or 5, preferably 1, 2 or 3, substituents.

Substituted aryl is preferably aryl substituted by at least one alkyl group ("alkaryl"). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-cyanophenyl.

The above remarks regarding unsubstituted or substituted aryl also apply to unsubstituted or substituted aryloxy and unsubstituted or substituted arylthio. Examples of aryloxy are phenoxy and naphthyloxy.

In the context of the present invention, hetaryl comprises heteroaromatic, mono- or polycyclic groups and monocyclic groups which may be fused to one or more unfused or fused saturated or unsaturated carbocyclic or heterocyclic five or six membered rings. In addition to the ring carbon atoms, these have 1, 2, 3, 4 or more than 4 of the ring heteroatoms. The heteroatoms are preferably selected from oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic hetaryl has 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl; benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl, dihydroisoquinolinyl.

Substituted heteroaryls may, depending on the number and size of their ring systems, have one or more (e.g. 1, 2, 3, 4, 5 or more than 5) substituents. These are preferably each independently selected from alkyl, alkoxy, alkylamino, alkylthio, cycloalkyl, heterocycloalkyl, aryl, hetaryl, fluorine, chlorine, bromine, cyano and nitro. Halogen substituents are preferably fluorine, chlorine or bromine. The substituents are preferably selected from $C_1$-$C_6$-alkyl, $C_1$-$C_6$-alkoxy, hydroxyl, carboxyl, halogen and cyano.

The above remarks regarding unsubstituted or substituted heteroaryl also apply to unsubstituted or substituted heteroaryloxy and unsubstituted or substituted heteroarylthio.

Halogen represents fluorine, chlorine, bromine or iodine, preferably chlorine and bromine. Alkali cation represents sodium, potassium, rubidium and cesium, preferably sodium and potassium.

R' in the tetraalkyl ammonium cation [NR']$^{4+}$ typically refers to methyl or tert.-butyl.

Further details on the preparation of the compounds according to the instant invention can be taken from the experimental section.

DSCs generally comprise the following elements: an electrically conductive layer (being part of or forming the working electrode or anode), a photosensitive layer generally comprising a semi-conductive metal oxide and a photosensitive dye, a charge transfer layer and another electrically conductive layer (being part of or forming the counter electrode or cathode).

Regarding further details of the construction of DSCs particular reference is made to WO 2012/001628 A1, which is hereby fully incorporated by reference.

EXPERIMENTAL PART

A1) Preparation of Compounds or General Formula I According to the Invention

Example 1

N-(1-ethylpropyl)-2,5-bis[3,3-dimethylbutyl]-8,11-bis[4,4,5,5-tetramethyl-1,3,2-dioxaborolan-2-yl]-perylene-3,4-dicarboxylic acid monoimide (C1)

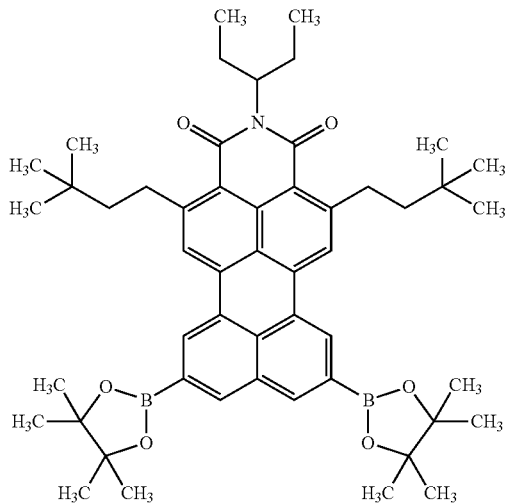 [SMILES: CCC(CC)N1C(=O)c2c(CCC(C)(C)C)cc3c4cc(B5OC(C)(C)C(C)(C)O5)cc5cc(B6OC(C)(C)C(C)(C)O6)cc(c6cc(CCC(C)(C)C)c(c2c36)C1=O)c54]

N-(1-ethylpropyl)-2,5-bis[3,3-dimethylbutyl]perylene-3,4-dicarboxylic acid monoimide (0.100 g, 0.179 mmol), bis(pinacolato)diboron (0.100 g, 0.393 mmol), [Ir(OMe)cod]$_2$ (bis(1,5-cyclooctadiene)dimethoxydiiridium; 5.9 mg, 8.9 μmol) and dtbpy (4,4'-di-tert-butyl-2,2'-bipyridyl; 4.8 mg, 17.9 μmol) were mixed in an oven dried flask under argon atmosphere. Anhydrous cyclohexane (3 ml) was added and the reaction heated for 1 hour at 80° C. in a microwave oven. After cooling down to room temperature, the solvent was evaporated and the solid purified by column chromatography (silica gel, first CH$_2$Cl$_2$/AcOEt 50/1 and afterwards CH$_2$Cl$_2$/acetone/MeOH 30/5/1). The desired compound C1 was obtained as an orange solid in 74% yield (0.107 g, 0.132 mmol).

$^1$H NMR (250 MHz, CD$_2$Cl$_2$) δ [ppm]: 8.78 (s, 2H), 8.40 (s, 2H), 8.26 (s, 2H), 5.19-4.99 (m, 1H), 3.47 (dt, J=24.7, 10.7 Hz, 4H), 2.44-2.16 (m, 2H), 2.00-1.77 (m, 2H), 1.65-1.52 (m, 4H), 1.44 (s, 24H), 1.09 (s, 18H), 0.92 (t, J=7.4 Hz, 6H).

$^{13}$C NMR (63 MHz, CD$_2$Cl$_2$) δ [ppm]: 165.41, 152.04, 139.48, 135.78, 133.66, 133.27, 131.54, 129.38, 129.15, 128.33, 125.38, 125.36, 119.57, 85.18, 57.55, 46.55, 33.15, 31.59, 30.00, 25.91, 25.56, 11.99.

FD Mass Spectrum (8 kV): m/z=815.0 (100%) [M+]

Example 2

N-(1-ethylpropyl)-8,11-bis[4,4,5,5-tetramethyl-1,3,2-dioxaborolan-2-yl]-perylene-3,4-dicarboxylic acid monoimide (C2)

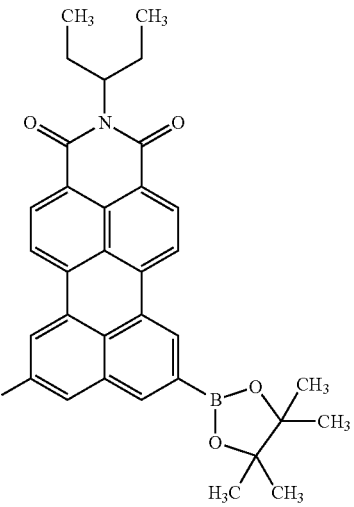

N-(1-ethylpropyl) perylene-3,4-dicarboxylic acid monoimide (2.00 g, 5.11 mmol), bispinacolondiboronate (3.11 g, 12.26 mmol), [Ir(OMe)cod]$_2$ (0.169 g, 0.255 mmol) and dtbpy (0.137 g, 0.511 mmol) were mixed in an oven dried flask under argon atmosphere. Anhydrous tetrahydrofuran (THF; 80 ml) was added and the reaction heated for 18 hours at 60° C. The solvent was evaporated and the reaction mixture dissolved in dichloromethane, precipitated in methanol and filtered. The process was repeated three times and the solid so obtained afterwards purified by GPC column (dichloromethane, Bio-Beads S-X1 Beads 200-400 mesh). The desired product C2 was obtained as a red solid (68% yield, 2.24 g, 3.47 mmol).

$^1$H NMR (250 MHz, CD$_2$Cl$_2$) δ [ppm]: 8.78 (s, 2H), 8.57-8.44 (m, 4H), 8.35 (s, 2H), 5.15-4.94 (m, 1H), 2.40-2.15 (m, 2H), 2.02-1.78 (m, 2H), 1.44 (s, 24H), 0.91 (t, J=7.5 Hz, 6H).

$^{13}$C NMR (63 MHz, CD$_2$Cl$_2$) δ [ppm]: 164.87, 139.54, 137.40, 133.52, 132.75, 131.16, 130.58, 129.90, 128.82, 128.24, 127.32, 121.72, 120.86, 84.97, 57.64, 25.56, 25.33, 11.71.

FD Mass Spectrum (8 kV): m/z=642.6 (100%) [M+]
UV-vis (in toluene): $\lambda_{max}$ ($\epsilon$ [M$^{-1}$ cm$^{-1}$]): 481 nm (2.98×10$^4$ M$^{-1}$ cm$^{-1}$), 509 nm (2.83×10$^4$ M$^{-1}$ cm$^{-1}$).

The monoborylated compound (also according to general formula I of the present invention)

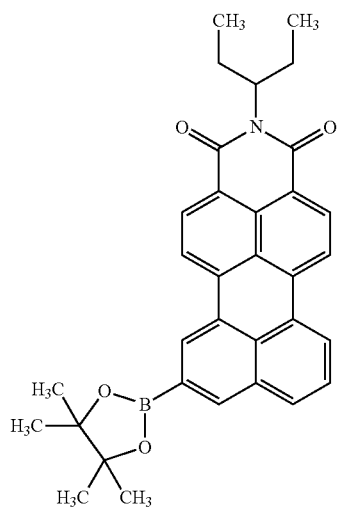

was obtained as by-product but not characterized further.

Example 3

N-(1-heptyloctyl)-8,11-bis[4,4,5,5-tetramethyl-1,3,2-dioxaborolan-2-yl]-perylene-3,4-dicarboxylic acid monoimide (C3)

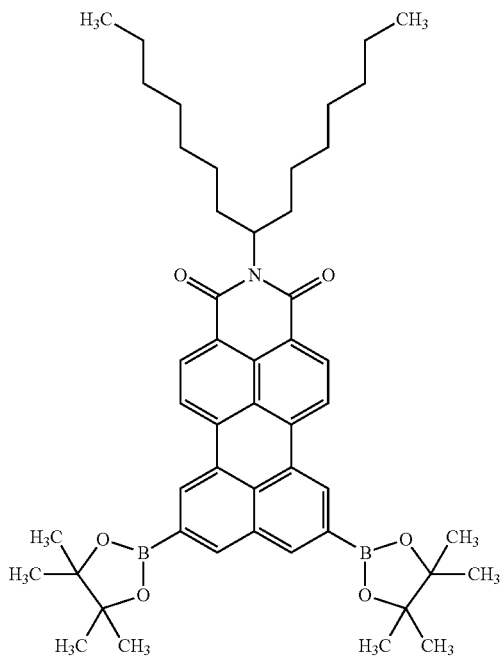

N-(1-heptyloctyl)-perylene-3,4-dicarboxylic acid monoimide (0.76 g, 1.42 mmol), bispinacolondiboronate (0.87 g, 3.43 mmol), [Ir(OMe)cod]2 (0.047 g, 0.255 mol) and dtbpy (0.137 g, 0.511 mmol) were mixed in an oven dried flask under argon atmosphere. Anhydrous THF (80 ml) was added and the reaction heated for 18 hours at 60° C. the solvent was evaporated and the reaction mixture dissolved in dichloromethane, precipitated in methanol and filtered. The process was repeated three times and the solid so obtained afterwards purified by GPC column (dichlormethane, Bio-Beads S-X1 Beads 200-400 mesh). The desired product C3 was obtained as a red solid (71% yield, 2.24 g, 3.47 mmol).

$^1$H NMR (250 MHz, CD$_2$Cl$_2$) δ [ppm]: 8.51 (s, 2H), 8.34 (d, J=5.5 Hz, 2H), 8.23 (d, J=8.2 Hz, 2H), 8.16 (s, 2H), 5.20 (tt, J=9.2, 5.9 Hz, 1H), 2.41-2.17 (m, 4H), 1.98-1.81 (m, 2H), 1.48 (s, 24H), 1.41-1.12 (m, 20H), 0.84 (t, J=6.6 Hz, 6H).

$^{13}$C NMR (63 MHz, CD$_2$Cl$_2$) δ [ppm]: 165.29, 164.35, 139.36, 137.04, 133.18, 131.87, 131.15, 130.75, 130.27, 129.55, 128.45, 128.12 126.97, 122.01, 121.21, 120.61, 84.93, 54.61, 32.98, 32.47, 30.24, 29.91, 27.67, 25.44, 23.24, 14.46.

A2) Preparation of Compounds or General Formula II According to the Invention:

Example 4

N-(1-ethylpropyl)perylene-8,11-bis-bromo-perylene-3,4-dicarboxylic acid monoimide (C4)

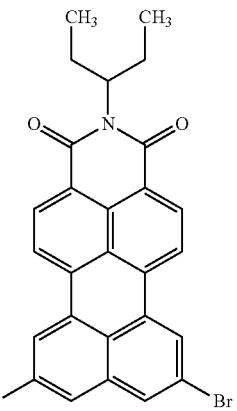

N-(1-ethylpropyl)-8,11-bis[4,4,5,5-tetramethyl-1,3,2-dioxaborolan-2-yl]-perylene-3,4-dicarboxylic acid monoimide (0.600 g, 0.933 mmol) was suspended in a mixture of dioxane (100 ml), methanol (10 ml) and water (10 ml) in a 210 mL pressure vial. Copper(II) bromide (2.08 g, 9.33 mmol) was added, the vessel sealed and heated up to 120° C. for 12 hours. The reaction mixture was poured into 200 mL of 1.0 M hydrochloric acid and filtered to obtain a red solid. The desired compound C4 was obtained after column chromatography (silica, toluene) and crystallization from toluene as an orange solid (yield 48%, 0.25 g, 0.48 mmol).

$^1$H NMR (500 MHz, 373 K, C$_2$Cl$_4$D$_2$) δ [ppm]: 8.64 (d, J=5.2 Hz, 2H), 8.50 (s, 2H), 8.43 (d, J=6.0 Hz, 2H), 7.98 (s, 2H), 5.20-4.94 (m, 1H), 2.35-2.21 (m, 2H), 2.08-1.95 (m, 2H), 1.03-0.96 (m, 6H).

$^{13}$C NMR (126 MHz, D$_2$SO$_4$) δ [ppm]: 164.68, 164.42, 148.77, 148.62, 145.82, 143.72, 143.53, 139.88, 138.98, 138.17, 135.49, 131.55, 128.93, 126.02, 125.57, 125.46, 125.39, 122.74, 112.08, 111.88, 71.63, 25.65, 11.14 (Signal at 11.14 set as reference using the chemical shift of the same carbon obtained from a $^{13}$C NMR in tetrachloroethane).

FD Mass Spectrum (8 kV): m/z=549.6 (100%) [M+]
UV-vis (in toluene): $\lambda_{max}$ ($\epsilon$ [M$^{-1}$ cm$^{-1}$]): 495 nm (3.21×10$^4$ M$^{-1}$ cm$^{-1}$), 466 nm (2.45×10$^4$ M$^{-1}$ cm$^{-1}$).

The monobrominated compound (also according to general formula II of the present invention)

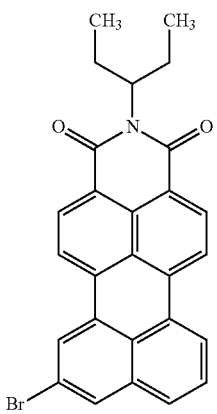

was obtained as by-product but not characterized further.

Example 5

N-(1-1-heptyloctyl)perylene-8,11-bis-bromo-perylene-3,4-dicarboxylic acid monoimide (C5)

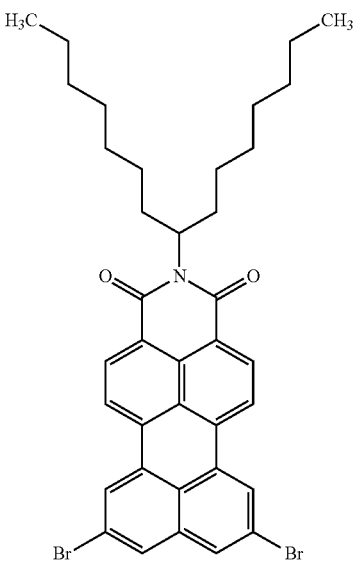 [SMILES: CCCCCCCC(CCCCCCC)N1C(=O)c2ccc3c4cc(Br)cc5cc(Br)cc(c6ccc(c2c36)C1=O)c54]

N-(1-heptyloctyl)-8,11-bis[4,4,5,5-tetramethyl-1,3,2-dioxaborolan-2-yl]-perylene-3,4-dicarboxylic acid monoimide (1.00 g, 1.28 mmol) was suspended in a mixture of THF (90 ml), methanol (10 ml) and water (10 ml) in a 210 mL pressure vial. Copper(II) bromide (2.85 g, 12.8 mmol) was added, the vessel sealed and heated up to 120° C. for 12 hours. The reaction mixture was poured into 200 mL of 1.0 M hydrochloric acid and filtered to obtain a red solid. The desired compound C5 was obtained after column chromatography (silica, toluene) and obtained as a bright orange solid (yield 38%, 0.34 g, 0.49 mmol).

$^1$H NMR (500 MHz, CD$_2$Cl$_2$) δ [ppm]: 8.32 (s, br, 2H), 7.80 (d, J=8.0 Hz, 2H), 7.73 (s, 2H), 7.35 (s, 2H), 5.21-5.06 (m, 1H), 2.31-2.17 (m, 2H), 1.94-1.77 (m, 2H), 1.42-1.20 (m, 20H), 0.86 (t, J=6.6 Hz, 6H)

$^{13}$C NMR (126 MHz, CD$_2$Cl$_2$) δ [ppm]: 164.97, 136.25, 134.15, 131.68, 131.11, 130.83, 129.68, 126.16, 126.11, 124.73, 123.44, 122.45, 121.23, 54.94, 32.94, 32.45, 30.16, 29.89, 27.73, 23.23, 14.45.

FD Mass Spectrum (8 kV): m/z=549.6 (100%) [M+]
UV-vis (in toluene): $\lambda_{max}$ ($\epsilon$ [M$^{-1}$ cm$^{-1}$]): 496 nm (3.68×10$^4$ M$^{-1}$ cm$^{-1}$), 467 nm (2.84×10$^4$ M$^{-1}$ cm$^{-1}$).

Example 6

N-(1-ethylpropyl)perylene-8,11-bis-chloro-perylene-3,4-dicarboxylic acid monoimide (C6)

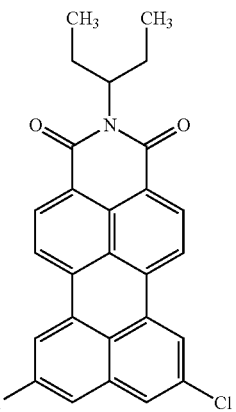

N-(1-ethylpropyl)-8,11-bis[4,4,5,5-tetramethyl-1,3,2-dioxaborolan-2-yl]-perylene-3,4-dicarboxylic acid monoimide (0.600 g, 0.933 mmol) was suspended in a mixture of dioxane (100 ml), methanol (10 ml) and water (10 ml) in a 210 mL pressure vial. Copper(II) chloride (1.254 g, 9.33 mmol) was added, the vessel sealed and heated up to 120° C. for 12 hours. The reaction mixture was poured into 200 mL of 1.0 M hydrochloric acid and filtered to obtain a red solid. The desired compound C6 was obtained after column chromatography (silica, toluene) and crystallization from toluene as a dark orange solid (yield 54%, 0.23 g, 0.50 mmol).

$^1$H NMR (250 MHz, C$_2$D$_2$Cl$_4$) δ [ppm]: 8.51 (d, J=8.0 Hz, 2H), 8.26 (d, J=8.2 Hz, 2H), 8.13 (d, J=1.7 Hz, 2H), 7.62 (d, J=1.5 Hz, 2H), 4.98 (d, J=6.0 Hz, 1H), 2.31-2.08 (m, 2H), 2.02-1.81 (m, 2H), 0.89 (t, J=7.4 Hz, 6H).

$^{13}$C NMR (126 MHz, D$_2$SO$_4$) δ [ppm]: 164.71, 164.44, 149.05, 148.92, 140.44, 138.95, 138.38, 138.12, 137.19, 135.23, 131.65, 128.97, 126.12, 125.49, 122.43, 112.07, 111.77, 71.79, 25.68, 11.15 (signal at 11.15 set as reference using the chemical shift of the same carbon obtained from a $^{13}$C NMR in tetrachloroethane).

FD Mass Spectrum (8 kV): m/z=460.6 (100%) [M+]
UV-vis (in toluene): $\lambda_{max}$ ($\epsilon$ [M$^{-1}$ cm$^{-1}$]): 494 nm (2.61×10$^4$ M$^{-1}$ cm$^{-1}$), 465 nm (2.00×10$^4$ M$^{-1}$ cm$^{-1}$).

The monochlorinated compound (also according to general formula II of the present invention)

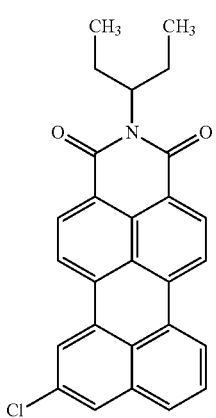

was obtained as by-product but not characterized further.

A3) Preparation of Compounds or General Formula III According to the Invention:

Example 7

N-(1-Ethylpropyl)-9-(bis(4-(2,4,4-trimethylpentane-2-yl)phenyl)amino-perylene-3,4-dicarboximide (C7)

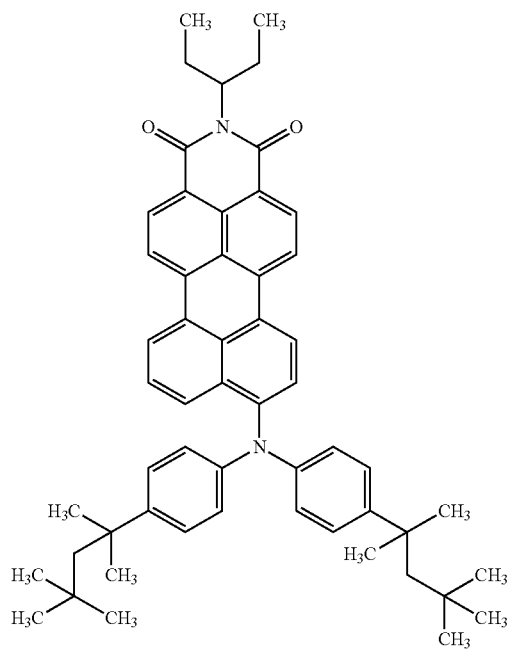 [SMILES: CCC(CC)N1C(=O)c2ccc3c4cccc5c(N(c6ccc(C(C)(C)CC(C)(C)C)cc6)c6ccc(C(C)(C)CC(C)(C)C)cc6)ccc(c6ccc(c2c36)C1=O)c54]

1.4 g of 9-(bis(4-(2,4,4-trimethylpentane-2-yl)phenyl) amino-perylene-3,4-dicarboxy anhydride (synthesis according to the procedure presented in Li, C. "Novel Functional Rylene Dyes for Dye-Sensitized Solar Cells", Ph.D. thesis, Johannes-Gutenberg-Universität Mainz, 2008), 684 mg of pentan-3-amine (7.86 mol) and 20 g of imidazole (0.29 mol) were mixed in a Schlenk tube and stirred under argon at 140° C. overnight. After cooling down dilute hydrochloric acid was added. The blue precipitate was filtered and washed with water. The crude product C7 was purified by column chromatography on silica gel with dichloromethane and petrol ether (3:2).

Yield: 1.4 g blue solid (91%)

$^1$H NMR (300 MHz, THF, 298 K) δ [ppm]: 8.51-8.36 (m, 6H), 7.88 (d, J=8.4, 1H), 7.38-7.12 (m, 6H), 6.87 (d, J=8.6, 4H), 5.05-4.88 (m, 1H), 2.29-2.07 (m, 2H), 1.88-1.69 (m, 2H), 1.33-1.16 (m, 12H), 0.78 (t, J=7.4, 6H), 0.66 (s, 18H).

$^{13}$C NMR (75 MHz, THF, 298 K) δ [ppm]: 147.30, 146.07, 144.01, 136.81, 136.72, 131.00, 129.97, 129.86, 129.82, 127.51, 127.01, 126.49, 126.38, 126.30, 126.20, 124.65, 123.94, 122.31, 120.13, 119.77, 56.85, 56.64, 37.88, 32.07, 31.21, 30.97, 10.66.

IR spectrum (ATR) λmax [cm$^{-1}$]=3034, 2953, 2874, 2691, 1652, 1593, 1566, 1500, 1457, 1349, 1268, 1246, 1197, 1085, 808, 751.

UV-Vis spectrum (CH$_2$Cl$_2$): λmax [nm] (ε [M$^{-1}$ cm$^{-1}$])=578 (30,907).

High Resolution Mass (ESI): [M]+: calculated: 782.481, found: 782.4789, discrepancy: −2.8 ppm. The triphenylamine moiety is losing an electron to form [M]+ as well as [M+H]+.

Elemental analysis (C$_{55}$H$_{62}$N$_2$O$_2$): calculated: 84.36% C, 7.98% H, 3.58% N, % S found: 84.25% C, 7.62% H, 3.75% N, % S.

Example 8

N-(1'-Ethylpropyl)-9,11-(bis(bis(4-(2,4,4-trimethylpentane-2-yl)phenyl)amino-perylene-3,4-dicarboximide (C8)

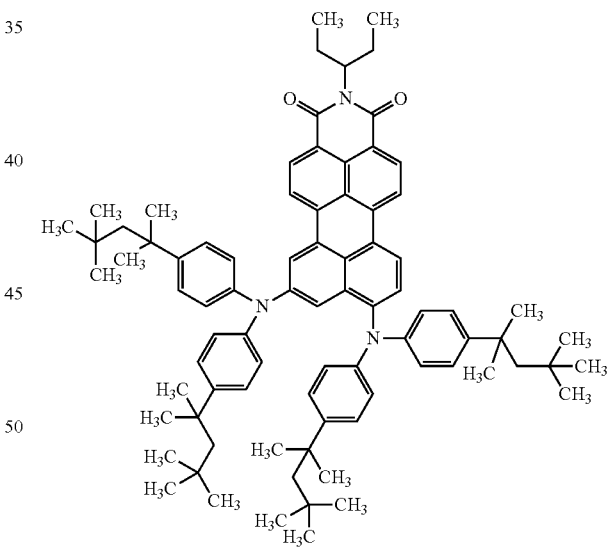

1 g of N-(1'-ethylpropyl)-9-(bis(4-(2,4,4-trimethylpentane-2-yl)phenyl)amino-perylene-3,4-dicarboximide (2.28 mmol) and 360 mg of 4,4,4',4',5,5,5',5'-octamethyl-2,2'-bi(1,3,2-dioxaborolane) (1.40 mmol), 42 mg of bis(1,5-cyclooctadiene) dimethoxydiiridium (0.065 mmol), and 34 mg of 4,4'-di-tert-butyl-2,2'-bipyridyl (0.119 mmol) were dissolved in 70 mL of dry THF under argon and stirred overnight at 60° C., however not leading to full conversion of the starting material. Both starting material and product show similar intensities on a silica thin layer chromatography plate in dichloromethane.

The solvent was removed under reduced pressure, the reaction mixture solved in dichloromethane, washed with water and dried over magnesium sulfate. It was then used without further purification for the next step.

900 mg of the mixture of N-(1'-ethylpropyl)-8-(4,4,5,5-tetramethyl-[1,3,2]dioxaborolan-2-yl)-10-(bis(4-(2,4,4-trimethylpentane-2-yl)phenyl)amino-perylene-3,4-dicarboximide and N-(1'-ethylpropyl)-9-(bis(4-(2,4,4-trimethylpentane-2-yl)phenyl)amino-perylene-3,4-dicarboximide were dissolved in 16 mL of 1,4-dioxane, 2 mL of methanol and 2 mL of water in a pressure vial. 1.1 g of copper(II)bromide (4.95 mmol) were added and the mixture was stirred over night at 120° C. After cooling down, the reaction mixture was roughly purified via column chromatography on silica gel with dichloromethane giving a mixture of N-(1'-ethylpropyl)-8-bromo-10-(bis(4-(2,4,4-trimethylpentane-2-yl)phenyl)amino-perylene-3,4-dicarboximide and N-(1'-ethylpropyl)-9-(bis(4-(2,4,4-trimethylpentane-2-yl)phenyl)amino-perylene-3,4-dicarboximide which was used directly for the next step.

150 mg of the mixture of N-(1'-ethylpropyl)-8-bromo-10-(bis(4-(2,4,4-trimethylpentane-2-yl)phenyl)amino-perylene-3,4-dicarboximide and N-(1'-ethylpropyl)-9-(bis-(4-(2,4,4-trimethylpentane-2-yl)phenyl)amino-perylene-3,4-dicarboximide, 65 mg of bis-(4-(2,4,4-trimethylpentane-2-yl)phenyl)-amine (0.165 mmol), 15 mg of sodium tert-butoxide (0.156 mmol), 21 mg of tris(dibenzylidenacetone) dipalladium(0) (0.023 mmol), and 10 mg of tri-tert-butylphosphine (0.050 mmol) were dissolved in 7 mL of dry toluene under argon and stirred at 80° C. overnight. The reaction mixture was purified via silica column chromatography with dichloromethane and petrol ether (2:1). Yield: 40 mg dark green solid compound C8.

$^1$H NMR (700 MHz, CD$_2$Cl$_2$, 298 K) δ [ppm]: 8.43 (d, J=7.5, 1H), 8.30-8.25 (m, 2H), 8.14 (d, J=8.2, 1H), 7.99 (d, J=1.6, 1H), 7.82 (d, J=8.1, 1H), 7.62 (d, J=1.5, 1H), 7.21-7.15 (m, 5H), 7.11 (d, J=8.7, 4H), 6.87 (d, J=8.5, 4H), 6.71 (d, J=8.6, 4H), 5.00-4.89 (m, 1H), 2.18-2.10 (m, 2H), 1.83-1.76 (m, 2H), 1.67 (s, 4H), 1.63 (s, 4H), 1.29 (s, 12H), 1.27 (s, 12H), 0.80 (t, J=7.4, 6H), 0.70 (s, 18H), 0.66 (s, 18H).

$^{13}$C NMR (126 MHz, CD$_2$Cl$_2$, 298 K) δ [ppm]: 147.3, 146.7, 146.6, 146.2, 144.6, 144.3, 137.5, 137.4, 133.6, 132.1, 130.7, 130.6, 129.0, 128.1, 127.0, 127.4, 127.0, 126.7, 125.5, 122.56, 122.42, 120.48, 120.39, 119.64, 115.26, 57.61, 57.48, 57.42, 38.79, 38.61, 32.86, 32.81, 32.16, 32.14, 31.0, 31.9, 30.3, 25.6, 11.7, 1.3.

IR spectrum (ATR) λmax [cm$^{-1}$]=2954, 2873, 1692, 1654, 1593, 1564, 1507, 1461, 1351, 1254, 1085, 1015, 805, 752.

UV-Vis spectrum (CH$_2$Cl$_2$): max [nm] (ε[M$^{-1}$ cm$^{-1}$])=612 (18,891).

High Resolution Mass (ESI): [M]+: calculated: 1173.8050, found: 1173.8015, discrepancy: −3.0 ppm. The triphenylamine moiety is losing an electron to form [M]+ as well as [M+H]+.

Elemental analysis (C$_{80}$H$_{95}$N$_3$O$_4$): calculated: 82.65% C, 8.24% H, 3.61% N, % S found: 81.66% C, 8.62% H, 3.68% N, % S.

Example 9

N-Carboxymethyl-8,10-bis(bis(4-(2,4,4-trimethylpentane-2-yl)phenyl)amino)perylene-3,4-dicarboximide (C9)

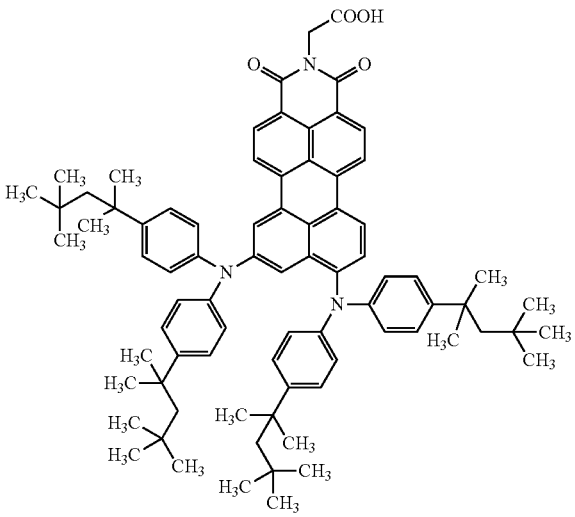 [SMILES: CC(C)(C)CC(C)(C)c1ccc(N(c2ccc(C(C)(C)CC(C)(C)C)cc2)c2cc3c(N(c4ccc(C(C)(C)CC(C)(C)C)cc4)c4ccc(C(C)(C)CC(C)(C)C)cc4)ccc4c5ccc6c7c(ccc(c(c2)c34)c75)C(=O)N(CC(=O)O)C6=O)cc1]

115 mg of N-(1'-ethylpropyl)-9,11-bis(bis(4-(2,4,4-trimethylpentane-2-yl)phenyl)amino) perylene-3,4-dicarboximide (0.097 mmol) were dissolved in 8 mL of 2-methyl-2-butanol and 4 mL of 1,4-dioxane. 219 mg of potassium hydroxide (3.92 mmol) were added, the reaction mixture desoxygenated and refluxed under argon overnight. The reaction mixture was poured into a ice water/acetic acid mixture (10:2). The precipitate was filtered, washed with water and after drying dissolved in dichloromethane. 1-2 mL of acetic acid were added and the solution was stirred for 1-2 days. After removal of the dichloromethane under reduced pressure, methanol was added. The precipitate was filtered and washed with methanol. The crude mixture was used directly for the next step. Yield (crude): 100 mg dark green solid (93%)

100 mg of 9,11-bis(bis(4-(2,4,4-trimethylpentane-2-yl)phenyl)amino)perylene-3,4-dicarboxy acid monoanhydride (0.094 mmol), 2 g of glycine (0.026 mol) and 3 g of imidazole (0.044 mol) were mixed in a Schlenk tube and stirred under argon at 140° C. overnight. After cooling down dilute hydrochloric acid was added. The brown precipitate was filtered and washed with water. The crude product was purified by column chromatography on silica gel with dichloromethane, THF, and acetic acid. Yield: 95 mg dark green solid (90%) of compound C9.

$^1$H-NMR (500 MHz, THF, 298 K) δ [ppm]: 8.47 (s, 2H), 8.38-8.30 (m, 2H), 8.15 (d, J=1.7, 1H), 7.97 (d, J=8.1, 1H), 7.78 (d, J=1.7, 1H), 7.33-7.20 (m, 9H), 6.96 (d, J=8.4, 4H), 6.83 (d, J=8.5, 4H), 4.78 (s, 2H), 1.77 (d, J=18.4, 8H, partially overlaid by solvent signal), 1.38 (d, J=7.9, 24H), 0.78 (d, J=15.2, 36H).

$^{13}$C-NMR (126 MHz, THF, 298 K) δ [ppm]: 163.7, 147.3, 147.0, 146.6, 145.2, 144.8, 138.0, 132.3, 131.8, 131.4, 131.0, 128.6, 128.4, 127.9, 127.6, 127.3, 126.3, 125.8, 123.7, 123.1, 122.0, 121.3, 121.1, 120.9, 58.0, 57.9, 39.2, 39.0, 33.3, 33.2, 32.5, 32.23.

IR spectrum (ATR) λmax [cm$^{-1}$]=2951, 2901, 2871, 1697, 1662, 1593, 1561, 1506, 1365, 1250, 1172, 1132, 1013, 821, 755.

UV-Vis spectrum (CH$_2$Cl$_2$) λmax [nm] (ε [M-1 cm-1])=631 (20,194).
High Resolution Mass (ESI) [M]+: calculated: 1161.7323, found: 1161.7336, discrepancy: 1.2 ppm. The triphenylamine moiety is losing an electron to form [M]+ as well as [M+H]+.

Example 10

N-(1'-Ethylpropyl)-8,11-bis(bis(9,9-dimethyl-9H-fluoren-2-yl)amino)perylene-3,4-dicarboximide
(C10)

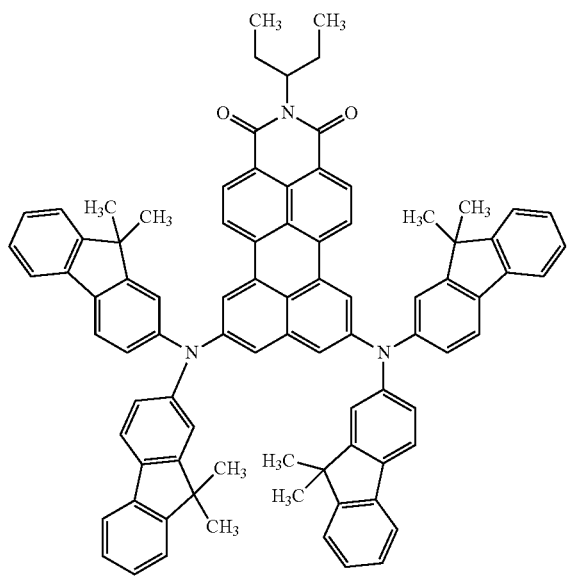 [SMILES: CCC(CC)N1C(=O)c2ccc3c4cc(N(c5ccc6c(c5)C(C)(C)c5ccccc5-6)c5ccc6c(c5)C(C)(C)c5ccccc5-6)cc5cc(N(c6ccc7c(c6)C(C)(C)c6ccccc6-7)c6ccc7c(c6)C(C)(C)c6ccccc6-7)cc(c6ccc(c2c36)C1=O)c54]

500 mg of N-(1'-ethylpropyl)-8,11-dichloro-perylene-3,4-dicarboximide (1.09 mmol), 960 mg of bis-(9,9-dimethylfluoren-2-yl)-amine (2.39 mmol), 1.42 g caesium carbonate (4.34 mmol), 198 mg of tris(dibenzylideneacetone)dipalladium(0) (0.216 mmol), and 271 mg of 2,2'-bis(diphenylphosphino)-1,1'-binaphthyl (0.436 mmol) were dissolved in 30 mL of anhydrous toluene in a Schlenk tube and stirred under argon at 100° C. for 16 h. Monofunctionalised (8-functionalised and 9-functionalised) and difunctionalised product (8,11-functionalised and 8,10-functionalised) was obtained.

The reaction mixture was purified via gel permeation chromatography to separate mono- and difunctionalised product with chloroform and via column chromatography with dichloromethane.

Yield: 50 mg brown solid (4%) of compound C10.
$^1$H-NMR (700 MHz, THF, 298 K) δ [ppm]: 8.44-8.37 (m, 4H), 8.27 (d, J=8.0, 2H), 7.68 (t, J=8.5, 8H), 7.44-7.38 (m, 10H), 7.27 (t, J=7.4, 4H), 7.24-7.18 (m, 8H), 5.06-4.97 (m, 1H), 2.29-2.18 (m, 2H), 1.89-1.76 (m, 2H), 1.40 (s, 24H), 0.85 (t, J=7.4, 6H).
UV-Vis spectrum (CH$_2$Cl$_2$) λmax [nm] (ε=M$^{-1}$ cm$^{-1}$])=486 (25,828), 563 (13,369).
High Resolution Mass (ESI) [M]+: calculated: 1189.5546, found: 1189.5527, discrepancy: -1.6 ppm. The triphenylamine moiety is losing an electron to form [M]+ as well as [M+H]+.
The compound N-(1'-Ethylpropyl)-8-(bis(9,9-dimethyl-9H-fluoren-2-yl)amino)perylene-3,4-dicarboximide

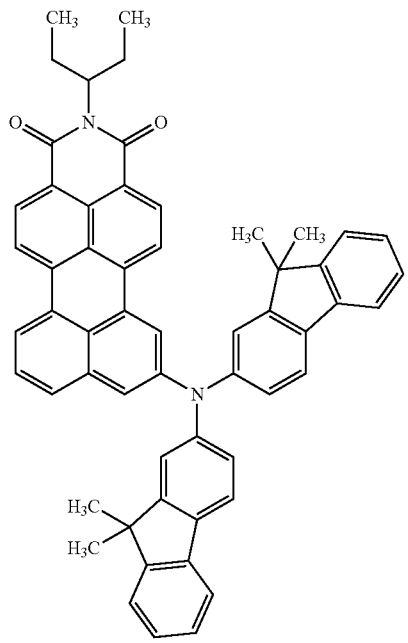 [SMILES: CCC(CC)N1C(=O)c2ccc3c4cccc5cc(N(c6ccc7c(c6)C(C)(C)c6ccccc6-7)c6ccc7c(c6)C(C)(C)c6ccccc6-7)cc(c6ccc(c2c36)C1=O)c54]

(also according to general formula III of the present invention) was obtained as by-product and characterized as follows.
Yield: 115 mg brownish-red solid (14%).
$^1$H-NMR (300 MHz, CD$_2$Cl$_2$, 298 K) δ [ppm]: 8.48 (d, J=8.0, 1H), 8.42 (d, J=2.1, 1H), 8.38-8.30 (m, 2H), 8.22 (d, J=7.1, 1H), 8.06 (d, J=8.2, 1H), 7.77-7.67 (m, 4H), 7.62 (d, J=8.0, 1H), 7.57 (d, J=1.9, 1H), 7.50 (d, J=7.7, 1H), 7.48-7.40 (m, 4H), 7.39-7.22 (m, 6H), 5.11-4.95 (m, 1H), 2.33-2.15 (m, 2H), 1.97-1.83 (m, 2H), 1.45 (s, 12H), 0.89 (t, J=7.5, 6H).
UV-Vis spectrum (CH$_2$Cl$_2$) λmax [nm] (ε=M$^{-1}$ cm$^{-1}$])=477 (23,629).
High Resolution Mass (ESI) [M]+: calculated: 790.3559, found: 790.3535, discrepancy: -3.1 ppm. The triphenylamine moiety is losing an electron to form [M]+ as well as [M+H]+.

Example 11

N-Carboxymethyl-8,11-bis(bis(9,9-dimethyl-9H-fluoren-2-yl)amino)perylene-3,4-dicarboximide
(C11)

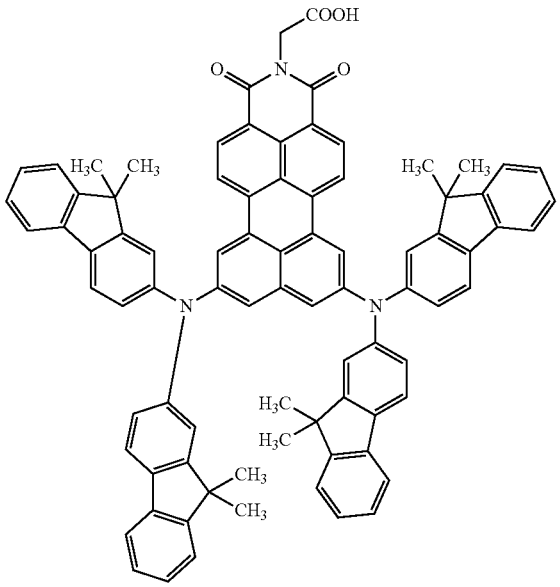 [SMILES: CC1(C)c2ccccc2-c2ccc(N(c3ccc4c(c3)C(C)(C)c3ccccc3-4)c3cc4cc(N(c5ccc6c(c5)C(C)(C)c5ccccc5-6)c5ccc6c(c5)C(C)(C)c5ccccc5-6)cc5c6ccc7c8c(ccc(c(c3)c45)c86)C(=O)N(CC(=O)O)C7=O)cc21]

50 mg of N-(1'-ethylpropyl)-8,11-bis(bis(9,9-dimethyl-9H-fluoren-2-yl)amino)perylene-3,4-dicarboximide (0.042 mmol) were dissolved in 4 mL of 2-methyl-2-butanol and 2 mL of 1,4-dioxane. 95 mg of potassium hydroxide (1.68 mmol) were added, the reaction mixture desoxygenated and reuxed under argon overnight. The reaction mixture was poured into a ice water/acetic acid mixture (10:2). The precipitate was filtered, washed with water and after drying dissolved in dichloromethane. 1-2 mL of acetic acid were added and the solution was stirred for 1-2 days. After removal of the dichloromethane under reduced pressure, methanol was added. The precipitate was filtered and washed with methanol. The crude mixture was used directly for the next step. Yield (crude): 45 mg red solid (94%)

45 mg of 8,11-bis(bis(9,9-dimethyl-9H-fluoren-2-yl)amino)perylene-3,4-dicarboxylic acid monoanhydride (0.036 mmol), 1 g of glycine (0.013 mol) and 2 g of imidazole (0.029 mol) were mixed in a Schlenk tube and stirred under argon at 140° C. overnight.

After cooling down dilute hydrochloric acid was added. The brown precipitate was filtered and washed with water. The crude product was purified by column chromatography on silica gel with dichloromethane, THF, and acetic acid. Yield: 40 mg red solid (85%) of compound C11.

$^1$H-NMR (300 MHz, THF, 298 K) δ [ppm]: 8.35-8.26 (m, 4H), 8.18 (d, J=8.2, 2H), 7.61-7.53 (m, 8H), 7.33-7.26, (m, 10H), 7.19-7.06 (m, 12H), 4.68 (s, 2H), 1.29 (s, 24H).

$^{13}$C-NMR (176 MHz, THF, 298 K) δ [ppm]: 169.8, 164.0, 156.6, 154.9, 148.9, 148.4, 140.2, 139.0, 137.9, 136.4, 132.5, 131.5, 131.2, 128.2, 128.1, 127.9, 124.8, 123.7, 123.1, 122.5, 122.3, 122.1, 122.0, 121.0, 120.7, 120.3, 48.1, 27.7, 26.2, 26.1.

UV-Vis spectrum (CH$_2$Cl$_2$) λmax [nm] (ε [M$^{-1}$ cm$^{-1}$])=477 (24,517), 574 (11,904).

IR spectrum (ATR) λmax [cm$^{-1}$]=3040, 2956, 2924, 2860, 1693, 1656, 1590, 1486, 1448, 1368, 1298, 1249, 1135, 1080, 1015, 966, 824, 777, 755, 734.

High Resolution Mass (ESI) [M]+: calculated: 1177.4819, found: 1177.4797, discrepancy: −1.8 ppm. The triphenylamine moiety is losing an electron to form [M]+ as well as [M+H]+.

Example 12

N-Carboxymethyl-8-(bis(9,9-dimethyl-9H-fluoren-2-yl)amino)perylene-3,4-dicarboximide (C12)

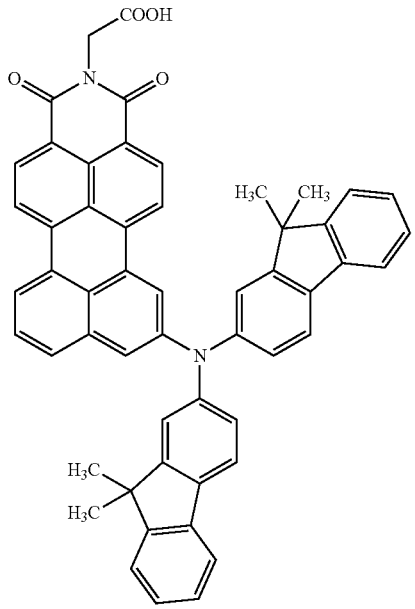 [SMILES: CC1(C)c2ccccc2-c2ccc(N(c3ccc4c(c3)C(C)(C)c3ccccc3-4)c3cc4cccc5c6ccc7c8c(ccc(c(c3)c45)c86)C(=O)N(CC(=O)O)C7=O)cc21]

96 mg of N-(1-ethylpropyl)-8-(bis(9,9-dimethyl-9H-fluoren-2-yl)amino)perylene-3,4-dicarboximide (0.122 mmol) were dissolved in 6 mL of 2-methyl-2-butanol and 3 mL of 1,4-dioxane. 255 mg of potassium hydroxide (4.55 mmol) were added, the reaction mixture desoxygenated and refluxed under argon overnight. The reaction mixture was poured into an ice water/acetic acid mixture (10:2). The precipitate was filtered, washed with water and after drying dissolved in dichloromethane. 1-2 mL of acetic acid were added and the solution was stirred for 1-2 days. After removal of the dichloromethane under reduced pressure, methanol was added. The precipitate was filtered and washed with methanol. The crude mixture was used directly for the next step. Yield (crude): 85 mg red solid (96%).

85 mg of 8-(bis(9,9-dimethyl-9H-uoren-2-yl)amino)perylene-3,4-dicarboxy monoanhydride (0.036 mmol), 1 g of glycine (0.013 mol) and 2 g of imidazole (0.029 mol) were mixed in a Schlenk tube and stirred under argon at 140° C. overnight. After cooling down dilute hydrochloric acid was added. The precipitate was filtered and washed with water. The crude product was purified by column chromatography on silica gel with dichloromethane, THF, and acetic acid. Yield: 80 mg red solid (87%) of compound C12.

$^1$H-NMR (300 MHz, THF, 298 K) δ [ppm]: 8.66-8.39 (m, 5H), 8.29 (d, J=8.2, 1H), 7.77-7.68 (m, 5H), 7.61 (d, J=1.8, 1H), 7.56 (t, J=7.9, 1H), 7.49-7.39 (m, 4H), 7.34-7.18 (m, 6H), 4.81 (s, 2H), 1.43 (s, 12H).

$^{13}$C-NMR (126 MHz, C$_2$Cl$_4$D$_2$, 393 K) δ [ppm]: 155.6, 153.8, 146.6, 138.6, 137.8, 135.3, 131.7, 129.9, 127.4, 126.9, 126.8, 123.7, 122.3, 122.1, 121.7, 120.9, 120.8, 120.2, 120.2, 119.5, 119.1, 46.8, 40.5, 26.9.

UV-Vis spectrum (CH$_2$Cl$_2$) λmax [nm] (ε[M$^{-1}$ cm$^{-1}$]) =484 (26,991).

IR spectrum (ATR) λmax [cm$^{-1}$]=3630, 3499, 3058, 2957, 2923, 2860, 1750, 1691, 1651, 1591, 1570, 1448, 1407, 1370, 1292, 1247, 1172, 1073, 1020, 970, 853, 799, 755, 736.

High Resolution Mass (ESI) [M]+: calculated: 778.2832, found: 778.2836, discrepancy: 0.6 ppm. The triphenylamine moiety is losing an electron to form [M]+ as well as [M+H]+.

Example 13

N-(1-heptyloctyl)-8,11-[2-nitrophenyl]-perylene-3,4-dicarboxylic acid monoimide (C13)

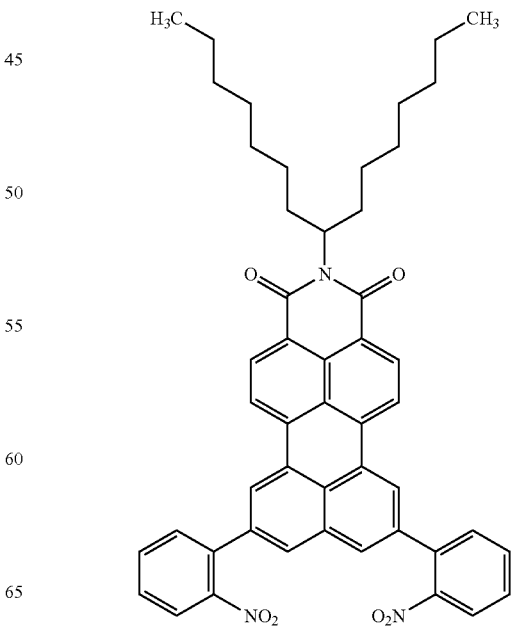

N-(1-heptyloctyl)-8,11-bis[4,4,5,5-tetramethyl-1,3,2-dioxaborolan-2-yl]-perylene-3,4-dicarboxylic acid (0.070 g, 0.09 mmol) and 1-bromo-2-nitrobenzene (0.054 g, 0.27 mmol) were mixed together and dissolved in 15 mL toluene and 0.15 mL ethanol. Potassium carbonate (148 mg, 1.07 mmol) was dissolved in 1.5 mL of water and added to the reaction mixture. After desoxygenation for 30 minutes, Pd(PPh$_3$)$_4$ (28 mg, 18 μmol) was added and the reaction mixture heated under argon atmosphere for 28 hours at 80° C. After cooling the reaction mixture to room temperature, the solvent was evaporated. The reaction mixture was dissolved in dichloromethane and filtered over silica. Finally the desired compound was obtained after gel permeation chromatography (BioBeads, THF). Yield: 82% (57 mg, 0.07 mmol) of compound C13.

$^1$H NMR (250 MHz, Methylene Chloride-d2) δ 8.46 (s, 2H), 8.44-8.29 (m, 4H), 8.04 (dt, J=8.1, 1.8 Hz, 2H), 7.86 (t, J=1.8 Hz, 2H), 7.83-7.73 (m, 2H), 7.73-7.58 (m, 4H), 5.15 (tt, J=9.1, 5.8 Hz, 1H), 2.34-2.12 (m, 1H), 1.94-1.74 (m, 2H), 1.38-1.11 (m, 20H), 0.82 (t, J=6.4 Hz, 6H).

$^{13}$C NMR (63 MHz, CD$_2$Cl$_2$) δ 149.50, 138.01, 136.38, 136.04, 134.82, 133.57, 132.88, 132.12, 131.37, 130.45, 130.35, 129.90, 129.70, 127.35, 127.26, 125.10, 124.33, 121.40, 54.78, 32.93, 32.38, 30.10, 29.80, 27.53, 23.18, 14.39.

FD Mass Spectrum (8 kV): m/z=773.9 (100%) [M+]

UV-vis (in CH$_2$Cl$_2$): λmax (ε [M$^{-1}$ cm$^{-1}$]): 476 nm (3.81×10$^4$ M$^{-1}$ cm$^{-1}$), 501 nm (4.20×10$^4$ M$^{-1}$ cm$^{-1}$).

Elemental Analysis: calculated: 76.05% C, 6.12% H, 5.43% N; experimental (%): 75.58% C, 6.41% H, 5.30% N.

B) Preparation and Characterization of the DSCs

General Methods and Materials

Preparation of the (solid-state) DSCs: A TiO$_2$ blocking layer was prepared on a fluorine-doped tin oxide (FTO)-covered glass substrate using spray pyrolysis (cf. B. Peng, G. Jungmann, C. Jager, D. Hearer, H. W. Schmidt, M. Thelakkat, Coord. Chem. Rev. 2004, 248, 1479). Next, a TiO$_2$ paste (Dyesol), diluted with terpineol, was applied by screen printing, resulting in a film thickness of 1.7 μm. All films were then sintered for 45 min at 450° C., followed by treatment in a 40 mM aqueous solution of TiCl$_4$ at 60° C. for 30 min, followed by another sintering step. The prepared samples with TiO$_2$ layers were pretreated with 5 mM solutions of the additive 2-(p-butoxyphenyl)acetohydroxamic acid sodium salt in ethanol (this additive is described on page 52 of WO 2012/001628 A1 as "Example No. 6"). The electrodes were then dyed in 0.5 mM dye solution in CH$_2$Cl$_2$. Spiro-MeOTAD was applied by spin-coating from a solution in DCM (200 mg/mL) also containing 20 mM Li(CF$_3$SO$_2$)$_2$N. Fabrication of the device was completed by evaporation of 200 nm of silver as the counter electrode. The active area of the sDSC was defined by the size of these contacts (0.13 cm$^2$), and the cells were masked by an aperture of the same area for measurements. The current-voltage characteristics for all cells were measured with a Keithley 2400 under 1000 W/m$^2$, AM 1.5G conditions (LOT ORIEL 450 W). The incident photon to current conversion efficiency's (IPCE) were obtained with an Acton Research Monochromator using additional white background light illumination.

The samples were illuminated with monochromatic light from the quartz monochromator with deuterium lamp. The power of the incident light beam was (2-5)·10$^{-8}$ W. The negative voltage of −300 V was supplied to the sample substrate. The counter-electrode with the 4.5×15 mm$^2$ slit for illumination was placed at 8 mm distance from the sample surface. The counter-electrode was connected to the input of the BK2-16 type electrometer, working in the open input regime, for the photocurrent measurement. The 10$^{-15}$-10$^{-12}$ A strong photocurrent was flowing in the circuit under illumination. The photocurrent J is strongly dependent on the incident light photon energy hv. The J$^{0.5}$=f(hv) dependence was plotted. Usually the dependence of the photocurrent on incident light quanta energy is well described by linear relationship between J$^{0.5}$ and hv near the threshold (cf. E. Miyamoto, Y. Yamaguchi, M. Yokoyama, Electrophotography 1989, 28, 364 and M. Cordona, L. Ley, Top. Appl. Phys. 1978, 26, 1). The linear part of this dependence was extrapolated to the hv axis and J$_p$ value was determined as the photon energy at the interception point.

The results of the DSCs with varying dyes/compounds are given in the following table 1.

TABLE 1

Photovoltaic performance of DSCs based on the compounds C9, C11 and C12

| Dye | EQE$_{max}$ [%] | V$_{oc}$ [mV] | I$_{sc}$ [mAcm$^{-2}$] | FF [%] | η [%] |
|---|---|---|---|---|---|
| C9 | 34 | 800 | −5.82 | 71 | 3.3 |
| C11 | 22 | 580 | −1.59 | 55 | 0.5 |
| C12 | 50 | 740 | −4.63 | 60 | 2.1 |

The invention claimed is:

1. A process for the preparation of compounds of general formula II

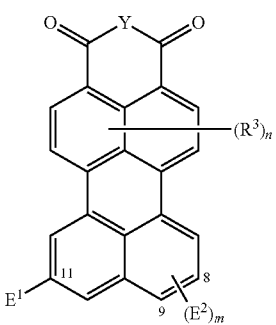

wherein the variables have the following meaning
Lg leaving group,
m 0 or 1, where in the case of m equal 1 the one Lg is bound either to the 8 or 9 position of the perylene skeleton and is identical to the Lg bound to the 11 position,
and the remaining variables R$^3$, n and Y have the meaning defined below, comprising reacting a compound of general formula I

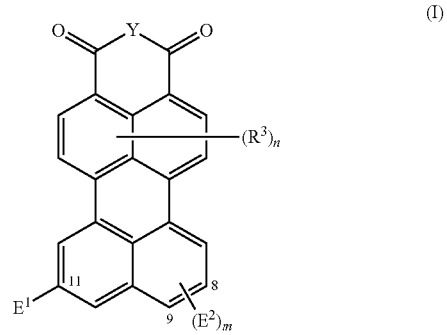

wherein the variables have the following meaning $E^1$, $E^2$ a moiety of formula Ia

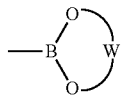
(Ia)

m 0 or 1, where in the case of m equal 1 $E^2$ is bound either to the 8 or 9 position of the perylene skeleton and is identical to $E^1$, W a bridging $C_2$ or $C_3$ moiety which may be substituted by one or more alkyl, $R^3$ identical or different radicals hydrogen, alkyl, cycloalkyl, aryl, hetaryl, alkoxy, aryloxy, arylthio, hetaryloxy, hetarylthio, diarylamino or dialkylamino, n 0, 1, 2, 3 or 4

Y oxygen or $NR^{12}$, and $R^{12}$ hydrogen, alkyl, cycloalkyl, aryl or hetaryl, or a moiety of formula —Z-A, wherein A is —COOM, —$SO_3M$ or —$PO_3M$ M hydrogen, alkali metal cation or $[NR']^{4+}$, R' hydrogen or alkyl, where the radicals R' may be identical or different, and Z is $C_1$-$C_6$-alkylene or 1,4-phenylene, where the phenylene radical may be substituted by one or more substituents alkyl, nitro, cyano and/or halogen with a compound $Cu(Lg)_2$ in the presence of a polar solvent under confined conditions and temperatures between 20° C. and 140° C.

2. A process according to claim 1 wherein in general formula II the variables have the following meaning Lg chlorine, bromine, iodine, brosylate, nosylate, tosylate, mesylate or triflate, m 0 or 1, where in the case of m equal 1 the one Lg is bound either to the 8 or 9 position of the perylene skeleton and is identical to the Lg bound to the 11 position.

3. Compounds of general formula II

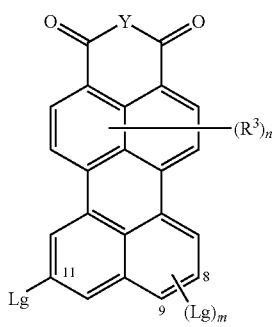
(II)

wherein the variables have the following meaning

Lg leaving group, m 0 or 1, where in the case of m equal 1 the one Lg is bound either to the 8 or 9 position of the perylene skeleton and is identical to the Lg bound to the 11 position, $R^3$ identical or different radicals hydrogen, alkyl, cycloalkyl, aryl, hetaryl, alkoxy, aryloxy, arylthio, hetaryloxy, hetarylthio, diarylamino or dialkylamino, n 0, 1, 2, 3 or 4

Y oxygen or $NR^{12}$, and $R^{12}$ hydrogen, alkyl, cycloalkyl, aryl or hetaryl, or a moiety of formula —Z-A, wherein A is —COOM, —$SO_3M$ or —$PO_3M$, M hydrogen, alkali metal cation or $[NR']^{4+}$, R' hydrogen or alkyl, where the radicals R' may be identical or different, Z $C_1$-$C_6$-alkylene or 1,4-phenylene, where the phenylene radical may be substituted by one or more substituents alkyl, nitro, cyano and/or halogen.

4. Compounds according to claim 3, wherein in general formula II the variables have the following meaning Lg chlorine, bromine, iodine, brosylate, nosylate, tosylate, mesylate or triflate, m 0 or 1, where in the case of m equal 1 the one Lg is bound either to the 8 or 9 position of the perylene skeleton and is identical to the Lg bound to the 11 position, $R^3$ identical or different radicals hydrogen, alkyl, cycloalkyl, aryl, alkoxy, aryloxy, diarylamino or dialkylamino, n 0, 1, 2, 3 or 4

Y oxygen or $NR^{12}$, and $R^{12}$ alkyl, or a moiety of formula —Z-A, wherein

A is —COOM,

M hydrogen, alkali metal cation or $[NR']^{4+}$,

R' hydrogen or alkyl, where the radicals R' may be identical or different,

Z $C_1$-$C_6$-alkylene or 1,4-phenylene.

5. A method of preparation of a dye-sensitized solar cell comprising combining a metal oxide with a compound of general formula II prepared according to claim 1.

6. A dye-sensitized solar cell comprising compounds of general formula II prepared according to claim 1.

* * * * *